United States Patent
Sanford et al.

(10) Patent No.: US 9,878,983 B2
(45) Date of Patent: Jan. 30, 2018

(54) PROCESS FOR FLUORINATING COMPOUNDS

(71) Applicants: Dow AgroSciences LLC, Indianapolis, IN (US); The Regents of the University of Michigan, Ann Arbor, MI (US)

(72) Inventors: Melanie Sanford, Ann Arbor, MI (US); Sarah Ryan, Ann Arbor, MI (US); Sydonie Schimler, Ann Arbor, MI (US); Yang Cheng, Midland, MI (US); Douglas Bland, Mason, OH (US)

(73) Assignees: Dow AgroSciences LLC, Indianapolis, IN (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/228,188

(22) Filed: Aug. 4, 2016

(65) Prior Publication Data
US 2017/0066721 A1   Mar. 9, 2017

Related U.S. Application Data

(60) Provisional application No. 62/200,983, filed on Aug. 4, 2015.

(51) Int. Cl.
| | |
|---|---|
| *C07D 213/79* | (2006.01) |
| *C07D 213/26* | (2006.01) |
| *C07D 213/76* | (2006.01) |
| *C07D 213/84* | (2006.01) |
| *C07D 213/85* | (2006.01) |
| *C07D 215/04* | (2006.01) |
| *C07D 217/02* | (2006.01) |
| *C07D 237/08* | (2006.01) |
| *C07D 213/803* | (2006.01) |

(52) U.S. Cl.
CPC ......... *C07D 213/79* (2013.01); *C07D 213/26* (2013.01); *C07D 213/76* (2013.01); *C07D 213/803* (2013.01); *C07D 213/84* (2013.01); *C07D 213/85* (2013.01); *C07D 215/04* (2013.01); *C07D 217/02* (2013.01); *C07D 237/08* (2013.01)

(58) Field of Classification Search
CPC .. C07D 213/26; C07D 213/76; C07D 213/79; C07D 213/803; C07D 213/84; C07D 213/85; C07D 215/04; C07D 217/02; C07D 237/08
See application file for complete search history.

(56) References Cited

U.S. PATENT DOCUMENTS

| | | |
|---|---|---|
| 6,274,770 B1 | 8/2001 | Clark et al. |
| 7,592,486 B2 | 9/2009 | Dimagno et al. |
| 7,939,697 B2 | 5/2011 | Hagiya |
| 2004/0144947 A1 | 7/2004 | Garayt et al. |
| 2006/0009963 A1 | 1/2006 | Pleschke et al. |
| 2011/0313170 A1 | 12/2011 | Dimagno et al. |
| 2012/0171653 A1 | 7/2012 | Kwon et al. |
| 2012/0190857 A1 | 7/2012 | Arndt et al. |
| 2012/0190858 A1 | 7/2012 | Zhu et al. |
| 2012/0190859 A1 | 7/2012 | Zhu et al. |
| 2012/0190860 A1 | 7/2012 | Whiteker et al. |
| 2014/0031556 A1 | 1/2014 | Renga et al. |
| 2014/0031558 A1 | 1/2014 | Renga et al. |
| 2014/0171650 A1 | 6/2014 | Giampietro et al. |
| 2014/0171653 A1 | 6/2014 | Renga et al. |
| 2014/0171654 A1 | 6/2014 | Johnson et al. |
| 2014/0206881 A1 | 7/2014 | Zhu et al. |
| 2014/0296533 A1 | 10/2014 | Renga et al. |
| 2015/0133672 A1 | 5/2015 | Allen et al. |
| 2015/0133673 A1 | 5/2015 | Sanford et al. |
| 2015/0141654 A1 | 5/2015 | Allen et al. |

FOREIGN PATENT DOCUMENTS

| | | |
|---|---|---|
| EP | 0146924 A2 | 12/1984 |
| EP | 1698606 A1 | 9/2006 |
| WO | 02092608 A2 | 11/2002 |
| WO | 03076366 A2 | 9/2003 |
| WO | 03106379 A1 | 12/2003 |
| WO | 2004048350 A2 | 6/2004 |
| WO | 2006055748 A2 | 5/2006 |
| WO | 2012163905 A1 | 12/2012 |

OTHER PUBLICATIONS

Boechat, et al., Fluorodenitrations using tetramethylammonium fluoride, Journal of the Chemical Society, Chemical Communications, (11), 921-2 (1993).*
Allen et al., Developing Efficient Nucleophilic Fluorination Methods and Application to Substituted Picolinate Esters. Org. Proc. Res. Dev. 18(8):1045-1054, 2014.
Allen et al., Mild Fluorination of Chloropyridines with in situ Generated Anhydrous Tetrabutylammonium Fluoride. J. Org. Chem. 17(12):5827-5833, 2014.
Anbarasan, et al., "Efficient Synthesis of Aryl Fluorides", 49:2219-2222, 2010.
Balz et al., On aromatic fluorine compounds, I.: A new process for their preparation. Ber. Deutsch. Chem. Ges., 60:1186, 1927.
Barnette, et al., "N-Fluoro-N-alkylsulfonamides: Useful Reagents for the Fluorination of Carbanions", 452-454, 1984.
Bobbio et al., Removal of Fluorine from and Introduction of Flourine into Polyhalopyridines: An Exercise in Nucleophilic Hetarenic Substitution. Eur. J. Chem. 11(6):1903-1910, 2005.
Cox, et al., "Anhydrous" Tetrabutylammonium Fluoride: A mild but highly efficient source of Nucleophilic Fluoride Ion, 3216-3219, 1984.
Differding, et al., "Nucleophilic Substitution Versus Electron Transfer: 2SN2 at Fluorine and Electron Transfer are competing and different pathways in electrophilic Fluorinations", , 3819-3822, 1991.

(Continued)

Primary Examiner — Erich A Leeser
(74) Attorney, Agent, or Firm — Meunier Carlin & Curfman, LLC

(57) ABSTRACT

Disclosed are mild temperature (e.g., from 0 to 80° C.) $S_NAr$ fluorinations of a variety of halide and sulfonate substituted aryl and heteroaryl substrates using $NMe_4F$.

35 Claims, 2 Drawing Sheets

(56) References Cited

OTHER PUBLICATIONS

Gallardo, et al., "Nucleophilic Aromatic Substitution for Heteroatom. An Oxidative Electrochemical Approach", J Org Chem, 125-137, 2001.
Heinz, et al., "A simple synthesis of tetraalkylammonium salts with functional anions", 12:1937, 1978.
Higgins, et al., "pKas of the conjugate acids of N-heterocyclic carbenes in water", Chem Commun. 47, 1559-1561, 2011.
Kim et al., New Method of Fluorination Using Potassium Fluoride in Ionic Liquid: Significantly Enhanced Reactivity of Fluoride and Improved Selectivity, J. Am. Chem. Soc., 124:10278-10279, 2002.
Kuduk, et al., "Tetrabutylammonium Salt Induced Denitration of Nitropyridines: Synthesis of Fluoro-, Hydroxy-, and Methoxypyridines",Org. Lett., pp. 578, 2005.
Liang et al., Introduction of Fluorine and Fluorine-Containing Functional Groups, Angewandte Chemie International Edition, 52:8214-8264, 2013.
Maggini, et al., "A General Procedure for the Fluorodenitration of Aromatic Substrates", J Org Chem, J. Org. Chem. 56(22):6406-6411, 1991.
Okamoto et al., Activity and behavior of imidazolium salts as a phase transfer catalyst for a liquid-liquid phase system, Tetrahedron Letters, 47:8055-8058, 2006.
Sagar et al., Synthetic studies towards the antiviral pyrazine derivative T-205. Proceedings of the 13th Electronic Conference on Synthetic Organic Chemistry Nov. 1-30, 13:1-3, 2009.
Sasson, et al., "Tetramethylammonium chloride as a selective and robust phase transfer catalyst in a solid-liquid halex reation: the role of water", Chem. Commun., 197-298, 1996.
Sharma et al., Instability of Anhydrous Tetra-N-alkylammonium Fluorides, J. Org. Chem., 48:2112-2114, 1983.
Sun et al., Anhydrous Tetrabutylammonium Fluoride, J. Am. Chem. Soc., 127:2050-2051, 2005.
Sun, et al., "Room-temperature nucleophilic aromatic fluorination: experimental and theoretical studies", pp. 2721, 2006.
Walsh, et al., "Mutation in an Auxin Receptor Homolog AFB5 and in SGT1b Confer Resistance to Synthetic Picolinate Auxins and Not to 2,4-Dichlorophenoxyacetic Acid or Indole-3-Acetic Acid in Arabidopsis", 13 pages, 2006.
Yamada et al., Convenient Electrophilic Fluorination of Functionalized Aryl and Heteroaryl Magnesium Reagents, Angew. Chem., Int. Ed., 49:2215-2218, 2010.
Zhong et al., Direct Formation of 2,3,5-Trichloropyridine and its Nucleophilic Displacement Reactions in Ionic Liquid. Synthetic Commun. 34(23):4301-4311, 2004.
International Search Report and Written Opinion, issued in International Application No. PCT/US2016/045624 dated Oct. 27, 2016.
International Search Report and Written Opinion, issued in International Application No. PCT/US14/65199, dated Jan. 30, 2015.
International Preliminary Report on Patentability issued in International Application No. PCT/US14/65199, dated May 26, 2016.
International Search Report and Written Opinion issued in International Application No. PCT/US14/65212, dated Mar. 31, 2015.
International Preliminary Report on Patentability issued in International Application No. PCT/US14/65212, dated May 26, 2016.
International Search Report and Written Opinion issued in International Application No. PCT/US14/65272, dated Jan. 30, 2015.
International Preliminary Report on Patentability issued in International Application No. PCT/US14/65272, dated May 26, 2016.
Office Action issued in related U.S. Appl. No. 14/539,696, dated Feb. 19, 2016.
Office Action issued in related U.S. Appl. No. 14/539,700, dated Mar. 17, 2015.
Office Action issued in related U.S. Appl. No. 14/539,613, dated Dec. 30, 2015.
Office Action issued in related U.S. Appl. No. 14/539,613, dated Aug. 23, 2016.

* cited by examiner

PROCESS FOR FLUORINATING COMPOUNDS

CROSS REFERENCE TO RELATED APPLICATIONS

This application claims the benefit of priority to U.S. Provisional Application Ser. No. 62/200,983, filed Aug. 4, 2015, which is incorporated by reference herein in its entirety.

FIELD

This application relates generally to methods of fluorinating compounds and to fluorinated compounds.

BACKGROUND

Fluorinated organic molecules are increasingly used in life science industries. The presence of a fluorine substituent can have positive effects on the biological properties of compounds. The substitution of a hydrogen atom with a fluorine atom in biologically active molecules often imparts improvements in bioavailability and/or metabolic stability. However, despite the importance of the incorporation of fluorine into organic molecules, there are relatively few selective and mild synthetic methods for C—F bond formation, particularly on process scale. Thus, synthetic techniques for fluorinating compounds are a significant area of interest.

One method for the industrial preparation of aryl and heteroaryl fluorides is nucleophilic aromatic fluorination ($S_NAr$) or halex fluorination (Adams, D. J.; et al., *Chem. Soc. Rev.* 1999; 28:225; Langlois, B.; et al., In *Industrial Chemistry Library*; Jean-Roger, D.; Serge, R., Eds.; Elsevier: 1996; pp 244-292). This involves the reaction of an electron-deficient (hetero)aryl chloride or nitroarene with a nucleophilic fluoride source to generate the corresponding aryl fluoride (Id.; Kuduk, S. D.; et al., *Org. Lett.* 2005; 7:577). Anhydrous alkali metal fluorides (MF) are most commonly employed as the fluoride source. However, these salts are poorly soluble in organic solvents; as a result, high temperatures and long reaction times are necessary to obtain high yields of the fluorinated products. The forcing conditions can limit the functional group tolerance of these reactions and result in the formation of undesired side products (Id.).

Tetrabutylammonium fluoride (TBAF) has been used as a highly nucleophilic fluoride—ion source to fluorinate a variety of substrates. This reagent is prepared by treating tetrabutylammonium cyanide with hexafluorobenzene in a solvent and under anhydrous conditions. The resultant TBAF (i.e., $TBAF_{anh}$ or TBAF*) can then be used to fluorinate certain substrates. See DiMagno, et al., *J. Am. Chem. Soc.* 2005, 127, 2050-2051; DiMagno et al. *Angew. Chem. Int. Ed.* 2006, 45, 2720-2725; Allen, L.; et al., *Org. Process. Res. Dev.* 2014, 18(8):1045-1055; Allen, L.; et al., *J. Org. Chem.* 2014, 79(12):5827-5833. Similarly, the combination of acid fluorides and N-heterocyclic carbenes (NHCs) produces anhydrous acyl azolium fluoride reagents that participate in room temperature $S_NAr$ fluorination (Ryan, S. J.; et al., *Org. Lett.* 2015; 17:1866; Tang, P.; et al., *J. Am. Chem. Soc.* 2011; 133:11482; Fujimoto, T.; et al., *Org. Process Res. Dev.* 2014; 18:1041; Fujimoto, T.; et al. *Org. Lett.* 2015; 17:544).

While these methods have been successful in certain systems, they have limitations, such as poor selectivity and reactivity for certain substrates. These methods also require the use of expensive stoichiometric reagents ($C_6F_6$, NHCs) that preclude implementation on an industrial scale. What is needed are new methods for fluorinating compounds, especially a wide variety of fluorinated compounds, and the methods and compounds disclosed herein address these and other needs.

SUMMARY

The subject matter disclosed herein relates to methods of making compositions and the compositions themselves. In particular, the subject matter disclosed herein generally relates to methods of fluorinating compounds and to fluorinated compounds. In certain specific aspects, disclosed herein are methods of fluorinating aryl or heteroaryl compounds and to fluorinated compounds. In certain specific aspects, disclosed herein are methods of preparing a fluorinated aryl or heteroaryl substrate that comprise combining tetramethylammonium fluoride and an aryl or heteroaryl substrate substituted with at least one chloro, bromo, iodo, nitro, or sulfonate, at from 0° C. to 80° C. The disclosed processes can be run in batch or as a continuous process. One advantage of the disclosed methods is that one or more of the steps can be conducted at or about room temperature and the selectivity of the reaction is relatively high.

Examples of heteroaryl substrate that can be used have Formula I-A or I-B:

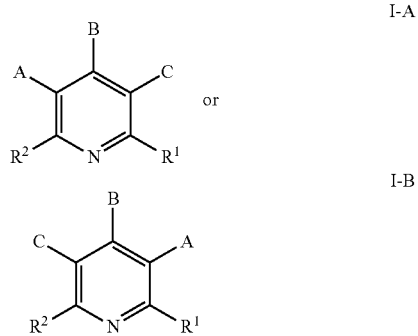

wherein
A is Cl, Br, I, $NO_2$, or $SO_3R^3$;
B is H, Cl, Br, I, $NO_2$, or $SO_3R^3$;
C is H, Cl, Br, I, $NO_2$, or $SO_3R^3$;
$R^1$ is H, CN, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, substituted or unsubstituted heteroaryl.

Further examples of heteroaryl substrates that can be used have Formula III-A:

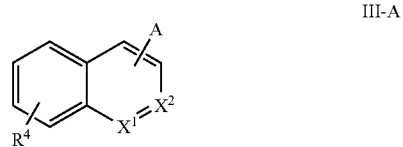

wherein
one of $X^1$ and $X^2$ is N and the other is C;
A is Cl, Br, I, $NO_2$, or $SO_3R^3$;
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^4$ is H, CN, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $OR^3$, $CO_2R^3$, substituted or unsubstituted aryl, substituted or unsubstituted heteroaryl.

Further examples of heteroaryl substrates that can be used have Formula IV-A:

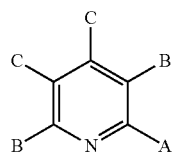

IV-A wherein
A is Cl, Br, I, $NO_2$, or $SO_3R^3$;
each B is, independent of the other, H, Cl, Br, I, $NO_2$, $SO_3R^3$, $SO_2R^3$, CN, $R^3$, $COR^3$, or $CO_2R^3$;
each C is, independent of the other, H, Cl, Br, I, $NO_2$, $SO_3R^3$, $SO_2R^3$, CN, $R^3$, $COR^3$, or $CO_2R^3$; and
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl.

Further examples of aryl substrates that can be used have Formula V-A:

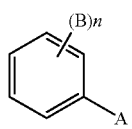

V-A wherein
A is Cl, Br, I, or $SO_3R^3$;
n is 0-5;
each B is, independent of any other, Cl, Br, I, CN, $SO_2R^3$, $R^3$, $COR^3$, or $CO_2R^3$;
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl.

Further examples of heteroaryl substrates that can be used can have Formula VI-A, VI-B, or VI-C:

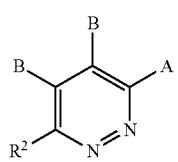

VI-A

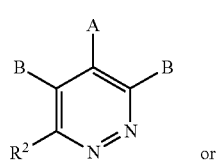

VI-B or

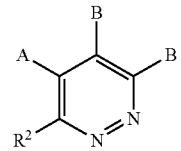

VI-C wherein
A is Cl, Br, I, $NO_2$, or $SO_3R^3$;
each B is independent of the other H, Cl, Br, I, CN, $NO_2$, $SO_2R^3$, $SO_2R^3$, $R^3$, $COR^3$, or $CO_2R^3$;
$R^2$ is H, substituted or unsubstituted aryl, substituted or unsubstituted heteroaryl;
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl.

Further examples of heteroaryl substrates that can be used can have Formula VII-A:

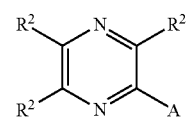

VII-A wherein
A is Cl, Br, I, $NO_2$, or $SO_3R^3$;
each $R^2$ is independent of one another H, halide, substituted or unsubstituted aryl, substituted or unsubstituted heteroaryl; and
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl.

Further examples of heteroaryl substrates that can be used have Formula VIII-A
A is Cl, Br, I, $NO_2$, or $SO_3R^3$;

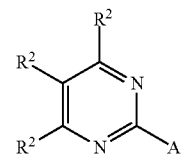

VIII-A each $R^2$ is independent of one another H, substituted or unsubstituted aryl, substituted or unsubstituted heteroaryl; and
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl.

In still other aspects, the subject matter disclosed herein relates to products prepared by the methods disclosed herein. In still other aspects, the subject matter disclosed herein relates to fluorinated compounds, such as those prepared by the disclosed methods.

Additional advantages of the disclosed subject matter will be set forth in part in the description that follows and the figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
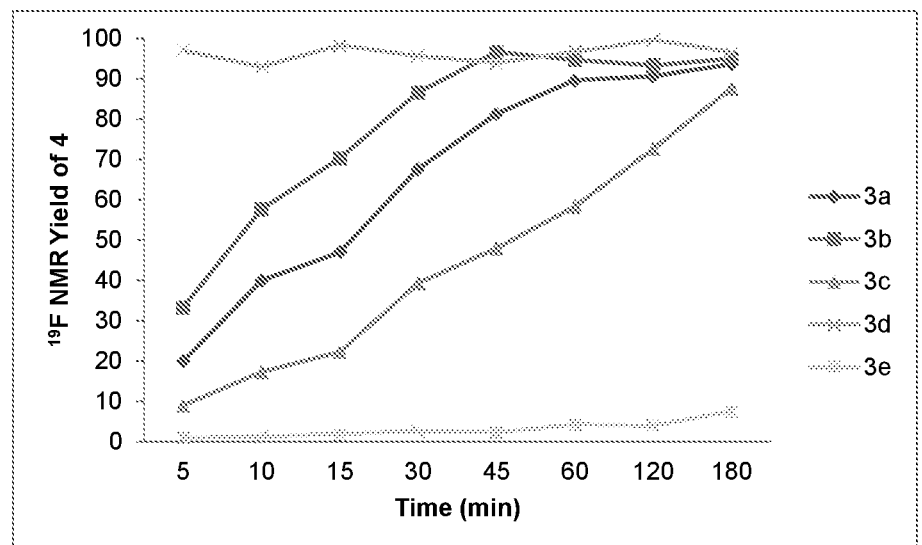
FIG. 1 is a graph showing reaction profiles for the reactions of 3a-e with anhydrous $NMe_4F$ to form 4. Conditions: substrate 3 (0.1 mmol, 1 equiv) and anhydrous $NMe_4F$ (0.2 mmol, 2 equiv) stirred in DMF (0.2 M) at 80° C. for the given time. Yields determined by $^{19}F$ NMR spectroscopy using 1,3,5-trifluorobenzene as a standard.

The materials, compounds, compositions, articles, and methods described herein may be understood more readily by reference to the following detailed description of specific aspects of the disclosed subject matter and the Examples and figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence upon which the reference is relied.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes a mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfonate, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ wherein $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E- and Z-isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfonate, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfonate, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfonate, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above wherein at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfonate, sulfoxide, or thiol as described herein. In certain specific examples cycloalkyl is a $C_{3-8}$ cycloalkyl.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," wherein at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfonate, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a shorthand notation for C=O, which is also referred to herein as a "carbonyl."

The terms "amine" or "amino" as used herein are represented by the formula —$NZ^1Z^2$, wherein $Z^1$ and $Z^2$ can each be a substituent group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NZ^1Z^2$.

The term "carboxylic acid" as used herein is represented by the formula —C(O)OH. A "carboxylate" or "carboxyl" group as used herein is represented by the formula —C(O)$O^-$.

The term "ester" as used herein is represented by the formula —OC(O)$Z^1$ or —C(O)O$Z^1$, wherein $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, wherein $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, wherein $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to fluorine, chlorine, bromine, and iodine. The corresponding term "halo", e.g., fluoro, chloro, bromo, and iodo as used herein refer to the corresponding radical or ion.

The term "hydroxyl" as used herein is represented by the formula —OH.

The term "cyano" as used herein is represented by the formula —CN. Cyanide is used to refer to the cyanide ion $CN^-$.

The term "nitro" as used herein is represented by the formula —$NO_2$.

The term "silyl" as used herein is represented by the formula —$SiZ^1Z^2Z^3$, wherein $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfooxo group represented by the formula —$S(O)_2Z^1$, wherein $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonate" is used herein to refer to the sulfooxo group represented by the formula —$OSO_2Z^1$, wherein $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

The term "thio" as used herein is represented by the formula —S—.

"$R^1$," "$R^2$," "$R^3$," "$R^n$," etc., wherein n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and figures.

Methods

Disclosed herein are methods of fluorinating certain substrates that use tetramethylammonium fluoride ($NMe_4F$) as a source of soluble anhydrous fluoride. $NMe_4F$ can offer certain advantages such as: (1) it can be prepared from inexpensive $NMe_4Cl$ and KF or $NMe_4OH$ and HF (Dermeik, S.; et al., *J. Org. Chem.* 1989; 54:4827; Tunder, R.; et al., *J. Inorg. Nucl. Chem.* 1963:25:1097; Christe, K. O.; et al., *J. Am. Chem. Soc.* 1990; 112:7619; EP 0457966 A1; DE1191813 B, which are incorporated herein in their entireties for their teachings of preparing $NMe_4F$); and (2) it can be rigorously dried at elevated temperatures (unlike $NBu_4F$, which is susceptible to elimination upon heating) (Sharma, R. K.; et al., *J. Org. Chem.* 1983; 48:2112). There are a few literature reports of the use of anhydrous $NMe_4F$ in (hetero) arene fluorination reactions. For instance, Grushin reported the fluorination of unactivated aryl bromides with $NMe_4F$ in DMSO at 90-110° C. (Grushin, V. V.; et al., *Organometallics* 2008; 27:4825). These reactions afforded mixtures of regioisomeric products in modest yields (10-65%), and an aryne mechanism was proposed for this transformation. Clark et al. have demonstrated numerous examples of $S_NAr$ fluorodenitration reactions of nitroarenes using anhydrous $NMe_4F$ (Boechat, N.; et al., *J. Chem. Soc., Chem. Commun.* 1993; 921; Adams, D. J.; et al., *J. Fluorine Chem.* 1998; 92:127; Clark, J. H.; et al. *J. Fluorine Chem.* 1995; 70:201; Clark, J. H.; et al., *Tetrahedron Lett.* 1993; 34:3901; Clark, J. H.; et al., *J. Chem. Res.* 1994; 478). These reactions are typically conducted at temperatures ranging from 60-100° C., and a variety of side products (e.g., arylethers, phenols) are formed in these systems (Id., Adams, D. J.; et al., *Tetrahedron* 1999; 55:7725; Adams, D. J.; et al., *J. Fluorine Chem.* 1999; 94:51; Maggini, M.; et al., *J. Org. Chem.* 1991; 56:6406). While fluorodenitration is well studied using $NMe_4F$, there are only a few reported examples of its use in $S_NAr$ halex reactions, and the substrate scope of such reactions has not been extensively explored (Id.; Filatov, A. A.; et al., *J. Fluorine Chem.* 2012; 143:123; Smyth, T.; et al., *Tetrahedron* 1995; 51:8901). Indeed, in many of these reports, the conversion of aryl chlorides to aryl fluorides was reported as an undesired side reaction of fluorodenitration reactions (Adams, D. J.; et al., *Tetrahedron* 1999; 55:7725; Adams, D. J.; et al., *J. Fluorine Chem.* 94:51, 1999). There are also relatively few systematic studies of the rate of $S_NAr$ fluorination reactions as a function of leaving group, and most of these have been conducted in context of radiofluorination (Karramakam, M.; et al., *Bioorg. Med. Chem.* 2003; 11:2769; Al-Labadi, A.; et al., *J. Radioanal. Nucl. Chem.* 2006; 270:313; Guo, N.; et al., *Appl. Radiat. Isot.* 2008; 66:1396; Dolci, L.; et al., *J. Labelled Compd. Radiopharm.* 1999; 42:975).

Disclosed herein are mild temperature (e.g., from 0 to 80° C.) $S_NAr$ fluorinations of a variety of halide and sulfonate substituted aryl and heteroaryl substrates using $NMe_4F$. It is shown that the reaction rates vary dramatically as a function of the leaving group, with nitroarenes and aryl bromides providing the fastest reactions. It is also shown that $NMe_4F$ can be used for the fluorination of a variety of industrially relevant chloropicolinates as well as other electron deficient (hetero)aromatic substrates. The reactions generally proceed in excellent yield, and the mild temperature limits the formation of side products derived from competing transesterification and/or deprotonation pathways. The disclosed methods comprise combining tetramethylammonium fluoride and an aryl or heteroaryl substrate substituted with at least one chloro, bromo, iodo, nitro, or sulfonate group. Examples of suitable sulfonate groups are triflate (OTf), mesylate, esylate, besylate, and tosylate, and the like.

The combination of the tetramethylammonium fluoride and the aryl or heteroaryl substrate can be accomplished by methods known in the art. For example, the tetramethylammonium fluoride can be added to the aryl or heteroaryl substrate. Typically, the addition can be accompanied by mixing, stirring, shaking or other form of agitation. Alternatively, the aryl or heteroaryl substrate can be added to the tetramethylammonium fluoride. Again this addition can be accompanied by mixing, stirring, shaking or other form of agitation. In still another example, the tetramethylammonium fluoride and aryl or heteroaryl substrate can be added together simultaneously. Any of these processes can be performed in a batch process or they can be a continuous process.

The amount of the tetramethylammonium fluoride can vary depending on the particular aryl or heteroaryl substrate. In certain examples, from 0.5 to 10 equivalents of the tetramethylammonium fluoride can be used per equivalent of the aryl or heteroaryl substrate. For example, from 0.5 to 9 equivalents, from 0.5 to 8 equivalents, from 0.5 to 7 equivalents, from 0.5 to 6 equivalents, from 0.5 to 5 equivalents, from 0.5 to 4 equivalents, from 0.5 to 3 equivalents, from 0.5 to 2 equivalents, from 1 to 10 equivalents, from 1 to 9 equivalents, from 1 to 8 equivalents, from 1 to 7 equivalents, from 1 to 6 equivalents, from 1 to 5 equivalents, from 1 to 4 equivalents, from 1 to 3 equivalents, from 1 to 2 equivalents, from 2 to 9 equivalents, from 2 to 8 equivalents, from 2 to 7 equivalents, from 2 to 6 equivalents, from 2 to 5 equivalents, from 2 to 4 equivalents, from 2 to 3 equivalents of the tetramethylammonium fluoride can be used per equivalent of the aryl or heteroaryl substrate. In some specific examples, from 0.5 to 5 equivalents, from 0.5 to 5 equivalents, or from 1 to 2 equivalents of the tetramethylammonium fluoride can be used per equivalent of the aryl or heteroaryl substrate.

The addition of these materials can be combined at temperatures from 0° C. to 80° C. For example, the tetramethylammonium fluoride and the aryl or heteroaryl substrate can be combined at above 0° C., above 10° C., above 20° C., above 30° C., above 40° C., above 50° C., above 60° C., or above 70° C. In other examples, the tetramethylammonium fluoride and the aryl or heteroaryl substrate can be combined at below 80° C., below 75° C., below 65° C., below 55° C., below 45° C., below 35° C., below 25° C., or below 15° C. In still other examples, the tetramethylammonium fluoride and aryl or heteroaryl substrate can be combined at 0, 5, 10, 15, 20, 25, 30, 35, 40, 45, 50, 55, 60, 65, 70, 75, or 80° where any of the stated values can form an upper or lower endpoint or a range. In still further examples, the tetramethylammonium fluoride and aryl or heteroaryl substrate can be combined at from 10° C. to 60° C., from 20° C. to 40° C., from 25° to 35° C., from 50° C. to 80° C., from 55° C. to 75° C., from 0° C. to 40° C., from 40° C. to 70° C., or from 15° C. to 50° C. In a specific example, the tetramethylammonium fluoride and the aryl or heteroaryl substrate can be combined at room temperature.

The tetramethylammonium fluoride and the aryl or heteroaryl substrate can be combined for from 1 minute to 24 hours. For example, the tetramethylammonium fluoride and the aryl or heteroaryl substrate can be combined for greater than 1 minute, greater than 15 minutes, greater than 30 minutes, greater than 1 hour, greater than 3 hours, greater than 5 hours, greater than 10 hours, greater than 15 hours, or greater than 20 hours. In other examples, the tetramethylammonium fluoride and the aryl or heteroaryl substrate can be combined for less than 24 hours, less than 20 hours, less than 12 hours, less than 8 hours, less than 6 hours, less than 4 hours, less than 2 hours, less than 45 minutes, or less than 20 minutes. In still other examples the tetramethylammonium fluoride and the aryl or heteroaryl substrate can be combined for 1 minute, 5 minutes, 10 minutes, 20 minutes, 40 minutes, 1 hours, 1.5 hours, 2 hours, 2.5 hours, 3 hours, 3.5 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours, where any of the stated values can form an upper or lower endpoint of a range. In still other examples, the tetramethylammonium fluoride and the aryl or heteroaryl substrate can be combined for from 1 minute to 3.5 hours, from 10 minutes to 2 hours, from 1 minute to 1 hour, or from 1 hour to 3 hours.

Solvents can also be used in the disclosed methods. For example, tetramethylammonium fluoride and the aryl or heteroaryl substrate can be combined in the presence of a solvent. Solvents can be added to the substrates or the tetramethylammonium fluoride, or any combination of these. Suitable solvents can be polar aprotic solvents. In certain examples, the solvent can be one or more of dimethylformamide (DMF), dimethylacetamide (DMAc), sulfolane, dimethylsulfoxide (DMSO), or deuterated analogs thereof. Other examples of solvents that can be used are tetrahydrofuran (THF), N-methylpyrrolidone (NMP), and benzonitrile. Any of these solvents alone or in combination with others solvents can be used in the methods disclosed herein.

If used in the disclosed methods, the amount of solvent can vary depending on the particular aryl or heteroaryl substrate. In certain examples, from about 0.5 to about 5 equivalents of the solvent can be used per equivalent of the aryl or heteroaryl substrate. For example, from about 0.5 to about 4.5 equivalents, from about 0.5 to about 4 equivalents, from about 0.5 to about 3.5 equivalents, from about 0.5 to about 3 equivalents, from about 0.5 to about 2.5 equivalents, from about 0.5 to about 2 equivalents, from about 0.5 to about 1.5 equivalents, from about 0.5 to about 1 equivalent, from about 1 to about 5 equivalents, from about 1 to about 4.5 equivalents, from about 1 to about 4 equivalents, from about 1 to about 3.5 equivalents, from about 1 to about 3 equivalents, from about 1 to about 2.5 equivalents, from about 1 to about 2 equivalents, from about 1 to about 1.5 equivalents, from about 1.5 to about 5 equivalents, from about 1.5 to about 4.5 equivalents, from about 1.5 to about 4 equivalents, from about 1.5 to about 3.5 equivalents, from about 1.5 to about 3 equivalents, from about 1.5 to about 2.5 equivalents, from about 1.5 to about 2 equivalents, from about 2 to about 5 equivalents, from about 2 to about 4.5 equivalents, from about 2 to about 4 equivalents, from about 2 to about 3.5 equivalents, from about 2 to about 3 equivalents, from about 2 to about 2.5 equivalents, from about 2.5 to about 5 equivalents, from about 2.5 to about 4.5 equivalents, from about 2.5 to about 4 equivalents, from about 2.5 to about 3.5 equivalents, from about 2.5 to about 3 equivalents, from about 3 to about 5 equivalents, from about 3 to about 4.5 equivalents, from about 3 to about 4 equivalents, from about 3 to about 3.5 equivalents, from about 3.5 to about 5 equivalents, from about 3.5 to about 4.5 equivalents, from about 3.5 to about 4 equivalents, from about 4 to about 5 equivalents, from about 4 to about 4.5 equivalents, or from about 4.5 to about 5 equivalents of the solvent can be used per equivalent of the aryl or heteroaryl substrate.

In some examples, the system comprising the tetramethylammonium fluoride, the aryl or heteroaryl substrate, and solvent (if present) is anhydrous. Thus, the tetramethylammonium fluoride can be anhydrous. The aryl and heteroaryl substrate can also be anhydrous. The solvent can also be anhydrous. The disclosed methods have, however, been found to tolerate the presence of water. Thus, in some examples herein, the tetramethylammonium fluoride, aryl or heteroaryl substrate, solvent, or any combination of these can contain water. For example, there can be up to 2 equivalents of water per equivalent of tetramethylammonium fluoride. In other examples, there can be up to 1.5 equivalents, 1 equivalent, 0.5 equivalent, or 0.1 equivalent of water per equivalent of tetramethylammonium fluoride.

In some specific examples of the disclosed methods, the tetramethylammonium fluoride and the aryl or heteroaryl substrate can be combined at about room temperature and in dimethylformamide.

Substrates

An advantage of the disclosed methods is that they can be effective at fluorinating a wide variety of substrates. It is particularly well suited for fluorinating aryl and heteroaryl substrates. In particular examples, the tetramethylammonium fluoride can be combined with the heteroaryl substrate and the heteroaryl substrate has Formula I-A or I-B:

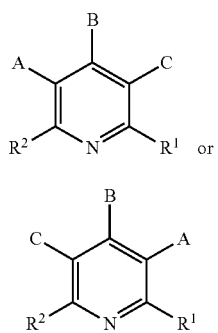

wherein
A is Cl, Br, I, $NO_2$, or $SO_3R^3$;
B is H, Cl, Br, I, $NO_2$, or $SO_3R^3$;
C is H, Cl, Br, I, $NO_2$, or $SO_3R^3$;
$R^1$ is H, CN, $SO_2R^3$, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, substituted or unsubstituted heteroaryl.

The resulting fluorinated product can have Formula II-A or II-B

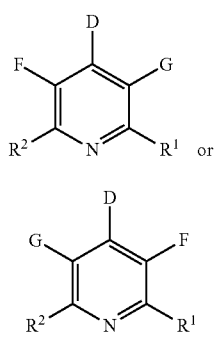

wherein D is B or F; and G is C or F.

In further examples, the tetramethylammonium fluoride can be combined with the heteroaryl substrate and the heteroaryl substrate has Formula III-A:

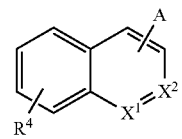

wherein
one of $X^1$ and $X^2$ is N and the other is CH or C-A;
A is Cl, Br, I, $NO_2$, or $SO_3R^3$;
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^4$ is H, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, CN, $SO_2R^3$, $OR^3$, $CO_2R^3$, substituted or unsubstituted aryl, substituted or unsubstituted heteroaryl. The resulting fluorinated product can be as noted in Formula III-A where A is replaced by F or as shown below in Formula III-B

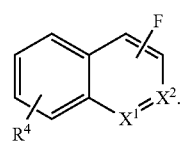

In still other examples, the tetramethylammonium fluoride can be combined with the heteroaryl substrate and the heteroaryl substrate has Formula IV-A:

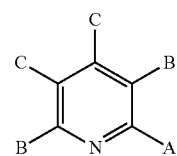

wherein
A is Cl, Br, I, $NO_2$, or $SO_3R^3$;
each B is independent of the other H, Cl, Br, I, $NO_2$, $SO_3R^3$, $SO_2R^3$, CN, $R^3$, $COR^3$, or $CO_2R^3$;
each C is independent of the other H, Cl, Br, I, $NO_2$, $SO_3R^3$, $SO_2R^3$, CN, $R^3$, $COR^3$, or $CO_2R^3$;
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl. The resulting fluorinated product can have Formula IV-B

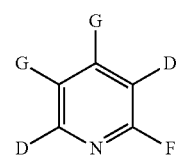

wherein each D is independently selected from B or F; and each G is independently selected from C or F. With these substrates, the fluorination can occur preferentially at the 2 position. So when any of B and C are Cl, Br, I, $NO_2$, $SO_3R^3$, the corresponding D and G group in the product is not F.

In yet further examples, the tetramethylammonium fluoride can be combined with the aryl substrate and the aryl substrate has Formula V-A:

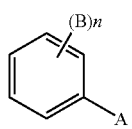

V-A wherein
A is Cl, Br, I, or $SO_3R^3$;
n is 0-5;
each B is, independent of any other, Cl, Br, I, CN, $SO_2R^3$, $R^3$, $COR^3$, or $CO_2R^3$;
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl. The resulting fluorinated product can have Formula V-B

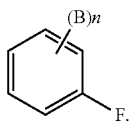

V-B

In still further examples, the tetramethylammonium fluoride can be combined with the heteroaryl substrate and the heteroaryl substrate can have Formula VI-A, VI-B, or VI-C:

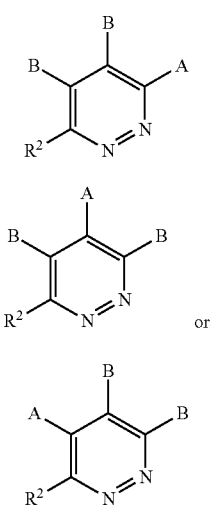

VI-A

VI-B or

VI-C wherein
A is Cl, Br, I, $NO_2$, or $SO_3R^3$;
each B is independent of the other H, Cl, Br, I, CN, $NO_2$, $SO_2R^3$, $SO_2R^3$, $R^3$, $COR^3$, or $CO_2R^3$;
$R^2$ is H, substituted or unsubstituted aryl, substituted or unsubstituted heteroaryl;

$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl. The resulting fluorinated product can have Formula VI-D, VI-E, or VI-F:

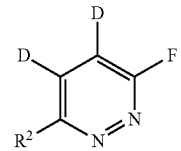

VI-D

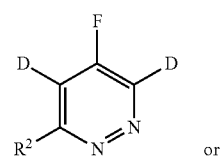

VI-E or

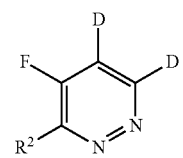

VI-F wherein each D is independently selected from B or F.

In still further examples, the tetramethylammonium fluoride can be combined with the heteroaryl substrate and the heteroaryl substrate can have Formula VII-A:

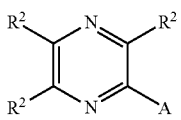

VII-A wherein
A is Cl, Br, I, $NO_2$, or $SO_3R^3$;
each $R^2$ is independent of one another H, halide, substituted or unsubstituted aryl, substituted or unsubstituted heteroaryl; and
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl.

The resulting fluorinated product can have Formula VII-B

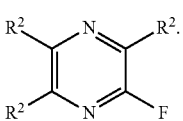

VII-B

In still further examples, the tetramethylammonium fluoride can be combined with the heteroaryl substrate and the heteroaryl substrate can have Formula VIII-A

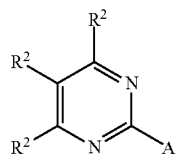

VIII-A

A is Cl, Br, I, NO₂, or SO₃R³;

each R² is independent of one another H, substituted or unsubstituted aryl, substituted or unsubstituted heteroaryl; and R³ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl.

In specific examples of the disclosed methods, NMe₄F was used for the $S_NAr$ fluorination of 5-chloropicolinate 1 (a structure motif found in US 2012-0190548; US 2012-0190860; US 2015-0025238; US 2012-0190549; US 2009-0088322; US 2007-0220629). This transformation was initially examined at temperatures ≥100° C., which are conditions commonly employed for $S_NAr$ fluorination (Adams, D. J.; et al., *Chem. Soc. Rev.* 1999; 28:225; Langlois, B.; et al., In *Industrial Chemistry Library*; Jean-Roger, D.; Serge, R., Eds.; Elsevier: 1996; pp 244-292; Allen, L. J.; et al., *Org. Process Res. Dev.* 2014; 18:1045). As shown in Table 1, the reaction of 1 with 2 equiv of anhydrous NMe₄F at 140° C. afforded complete conversion of 1 but only 66% yield of the fluoropicolinate product 2 (entry 1). Similarly at 100° C., the conversion of 1 was quantitative, but the yield of 2 was only 74%. The major side products observed in these transformations are the carboxylic acid 2-CO₂H and the iso-propyl ether 1-iPrO (Scheme 1).

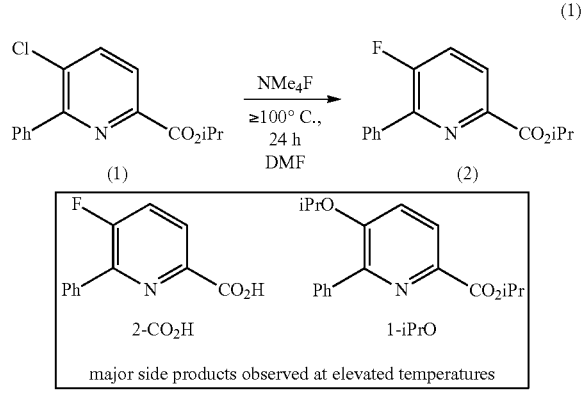

major side products observed at elevated temperatures

When the reaction temperature was lowered, e.g., to room temperature, full conversion of 1, along with quantitative yield of 2 (entry 5), was observed. Furthermore, with only 1 equiv of anhydrous NMe₄F, the $S_NAr$ fluorination of 1 proceeded to 80% yield at room temperature (entry 7). These results demonstrate that anhydrous NMe₄F has comparable reactivity to previously reported anhydrous NBu₄F (Allen, L. J.; et al., *J. Org. Chem.* 2014; 79:5827) and acyl azolium fluoride (Ryan, S. J.; et al. *Org. Lett.* 2015; 17:1866) reagents.

TABLE 1

$S_NAr$ Fluorination of 1 with Anhydrous NMe₄F

| entry[a] | equiv NMe₄F | temperature (° C.) | Conversion | yield[b] |
|---|---|---|---|---|
| 1 | 2 | 140° C. | 100% | 66% |
| 2 | 2 | 100° C. | 100% | 73% |
| 3 | 2 | 60° C. | 100% | 85% |
| 4 | 2 | 40° C. | 100% | 95% |
| 5 | 2 | Rt | 100% | 99% |
| 6 | 2[c] | Rt | 0% | <1% |
| 7 | 1 | Rt | 80% | 80% |

[a]Conditions: Substrate 1 (0.1 mmol) and anhydrous NMe₄F were stirred in DMF for 24 h.
[b]Yield determined by ¹⁹F NMR spectroscopy using 1,3,5-trifluorobenzene as a standard.
[c]NMe₄F · 4H₂O was used in place of anhydrous NMe₄F.

The use of NMe₄F•4H₂O under otherwise analogous conditions afforded none of the fluorinated product (Table 1, entry 6). Based on this result, the effect of H₂O on the room temperature reaction of 1 with 2 equiv of anhydrous NMe₄F was explored. In this study, various quantities of water were added to reactions that were set up under anhydrous conditions (Table 2). The addition of 1 equiv of water resulted in an approximately 25% reduction in the reaction yield (from 99% to 76%; entries 1 and 2, respectively). However, the addition of ≥2 equiv of water shut down the reaction, and <1% yield of 2 was observed under these conditions (entries 3 and 4). Bifluoride (HF₂) was the major species detected by ¹⁹F NMR spectroscopic analysis at the end of the reaction (¹⁹F NMR resonance at -152.0 ppm in CH₂Cl₂).

TABLE 2

Effect of Water on the Reaction of 1 with NMe₄F

| entry[a] | equiv H₂O | yield[b] |
|---|---|---|
| 1 | 0 | 99% |
| 2 | 1 | 76% |
| 3 | 2 | 1% |
| 4 | 5 | <1% |

[a]Conditions: Substrate 1 (0.1 mmol) and anhydrous NMe₄F (0.2 mmol) were combined to a 4 mL vial. DMF (0.2 M) and water were combined and added as a solution to the solids. The reaction was stirred at room temperature for 24 h.
[b]Yield was determined by ¹⁹F NMR spectroscopy using 1,3,5-trifluorobenzene as an internal standard.

The scope of aryl-X (X=Cl, Br, I, OTf, NO$_2$) substrates for the S$_N$Ar fluorination with anhydrous NMe$_4$F was also examined. A series of commercially available 2-substituted-benzonitrile substrates 3a-e were used. Compounds 3a-e react slowly with 2 equiv of anhydrous NMe$_4$F at room temperature, affording yields of 4 ranging from 2 to 98% after 48 h (Table 2). In most cases, significantly faster rates were observed at 80° C., and 3a-d afforded 4 in 88-99% yield after 3 h at 80° C. (Table 2, entries 1-4). In contrast, aryl triflate 3e showed minimal reactivity at 80° C., even at reaction times up to 48 h (entry 5). Time studies were conducted to obtain more detailed insight into the relative rates of fluorination of substrates 3a-e. As shown in FIG. 1, the relative rates were NO$_2$>>Br>Cl>I>>OTf. 2-Nitrobenzonitrile 3d reacted to afford nearly quantitative yield of 4 in just 5 min at 80° C., while all three of the halide substrates afforded quantitative conversion within 3 h under otherwise analogous conditions.

The reactions of 3a-e with anhydrous NMe$_4$F were compared to those with CsF, a more traditional reagent for S$_N$Ar fluorination. At 80° C., CsF afforded <5% yield of 4 in all cases. At 140° C. (more typical conditions for CsF halex reactions) (JP 2011153115 A; WO 2010018857; WO 2009014100; Hyohdoh, I.; et al., ACS Med. Chem. Lett. 2013; 4:1059; Finger, G. C.; et al., J. Am. Chem. Soc. 1956; 78:6034), the aryl halides 3a-c reacted with CsF to afford 4 in moderate 22-52% yield (entries 1-3). In all of these cases, unreacted starting material remained after 24 h at 140° C.

2-Nitrobenzonitrile 3d yielded 4 in 73% yield at 140° C., which is significantly lower than that obtained with NMe$_4$F. A variety of side products (most significantly ether derivatives) were detected by GCMS. These side products are common in fluorodenitration reactions as the displaced nitrite ion can act as a nucleophile (Boechat, N.; et al., J. Chem. Soc., Chem. Commun. 1993; 921; Adams, D. J.; et al., J. Fluorine Chem. 1998; 92:127; Clark, J. H.; et al., J. Fluorine Chem. 1995; 70:2011; Clark, J. H.; et al., Tetrahedron Lett. 1993; 34:3901; Clark, J. H.; et al., J. Chem. Res. 1994; 478; Adams, D. J.; et al., Tetrahedron 1999; 55:7725; Adams, D. J.; et al., J. Fluorine Chem. 1999; 94:51; Maggini, M.; et al., J. Org. Chem. 1991; 56:6406). In contrast, aryl triflate 3e afforded a significantly better yield with CsF at 140° C. (76%) than with NMe$_4$F at 80° C. (8%). These results highlight the advantages of the current method as well as its complementarity to other S$_N$Ar fluorination processes.

TABLE 3

S$_N$Ar Fluorination of Substrates 3a-e with Anhydrous NMe$_4$F

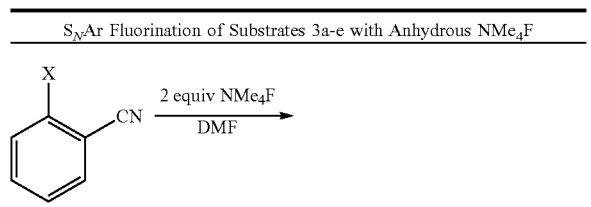

X = Cl (3a)
X = Br (3b)
X = I (3c)
X = NO$_2$ (3d)
X = OTf (3e)

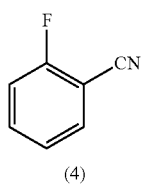

(4)

TABLE 3-continued

| entry | substrate | yield (24 h, 25° C.)$^a$ | yield (3 h, 80° C.)$^b$ | yield (CsF)$^c$ |
|---|---|---|---|---|
| 1 | 3a | 32% | 94% | 52% |
| 2 | 3b | 48% | 95% | 49% |
| 3 | 3c | 8% | 88% | 22% |
| 4 | 3d | 95% | 97% | 73% |
| 5 | 3e | 2% | 8% | 73% |

$^a$Conditions: Substrate (0.1 mmol) and anhydrous NMe$_4$F (0.2 mmol) stirred in DMF (0.2 M) at 25° C. for 24 h.
$^b$Conditions: Substrate (0.1 mmol) and anhydrous NMe$_4$F (0.2 mmol) stirred in DMF (0.2 M) at 80° C. for 3 h.
$^c$Conditions: Substrate (0.1 mmol) and CsF (0.2 mmol) stirred in DMF (0.2 M) at 140° C. for 24 h. All yields were determined by $^{19}$F NMR spectroscopy using 1,3,5-trifluorobenzene as an internal standard.

An analogous series of studies was conducted with the 2-substituted pyridine substrates 5a-c (Finger, G. C.; et al., J. Org. Chem. 1963; 28:1666). Similar to the results using 3a-e, the reactions of 2-chloro, 2-bromo, 2-iodo, and 2-nitropyridine (5a-d) with anhydrous NMe$_4$F at 80° C. afforded 2-fluoropyridine 6 in good to excellent yield (72-98%) (Table 4, entries 1-4). In all of these cases, the results compare favorably to those obtained under traditional halex conditions (2 equiv CsF, 140° C.; 9-100% yield for 5a-d; Table 4). Pyridin-2-yl trifluoromethanesulfonate (5e) underwent fluorination with anhydrous NMe$_4$F to afford 6 in moderate 43% yield. With this substrate, side products (most significantly ether derivatives) were detected by GCMS.

TABLE 4

S$_N$Ar Fluorination of Substrates 5a-e with Anhydrous NMe$_4$F.

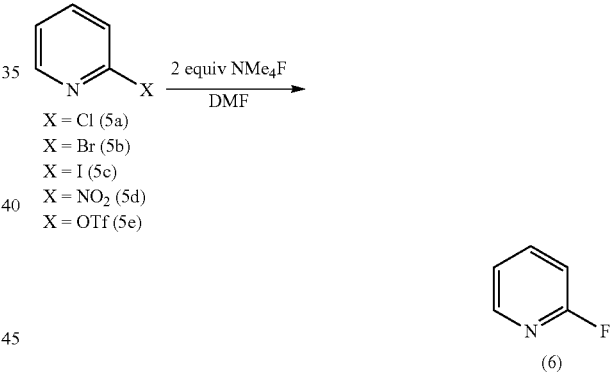

X = Cl (5a)
X = Br (5b)
X = I (5c)
X = NO$_2$ (5d)
X = OTf (5e)

(6)

| entry | substrate | yield (4 h, 80° C.)$^a$ | yield (CsF)$^b$ |
|---|---|---|---|
| 1 | 5a | 72% | 9% |
| 2 | 5b | 96% | 17% |
| 3 | 5c | 91% | 19% |
| 4 | 5d | 98% | 100% |
| 5 | 5e | 43% | 87% |

$^a$Conditions: Substrate (0.1 mmol) and anhydrous NMe$_4$F (0.2 mmol) stirred in DMF (0.2 M) at 80° C. for 4.
$^b$Conditions: Substrate (0.1 mmol) and CsF (0.2 mmol) stirred in DMF (0.2 M) at 140° C. for 24 h. All yields were determined by $^{19}$F NMR spectroscopy using 1,3,5-trifluorobenzene as an internal standard.

Figure 2:
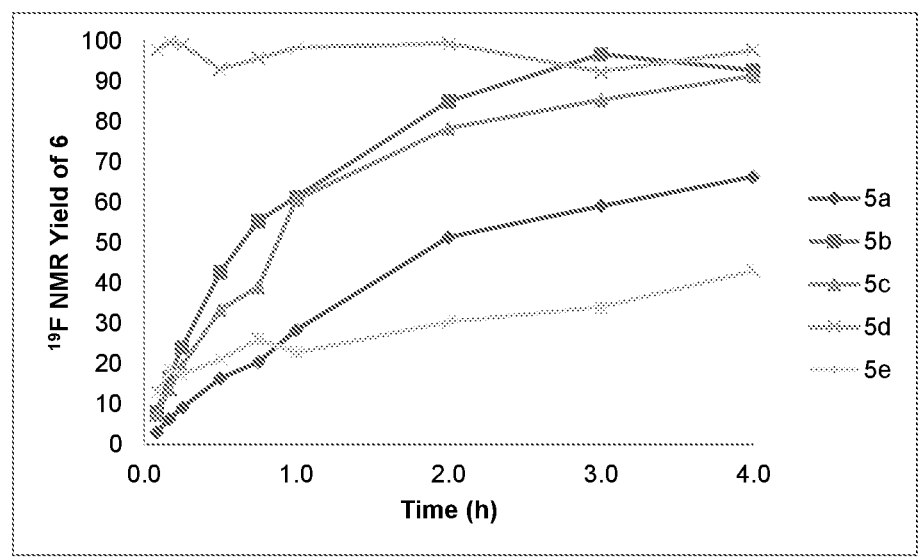
FIG. 2 is a graph showing reaction profiles for the reaction 5a-e with anhydrous $NMe_4F$ to form 6. General conditions: Substrate (0.1 mmol, 1 equiv) and anhydrous $NMe_4F$ (0.2 mmol, 2 equiv) stirred in DMF (0.2 M) at 80° C. for the given time. Yield was determined by $^{19}F$ NMR spectroscopy using 1,3,5-trifluorobenzene as a standard.
Figure 3:
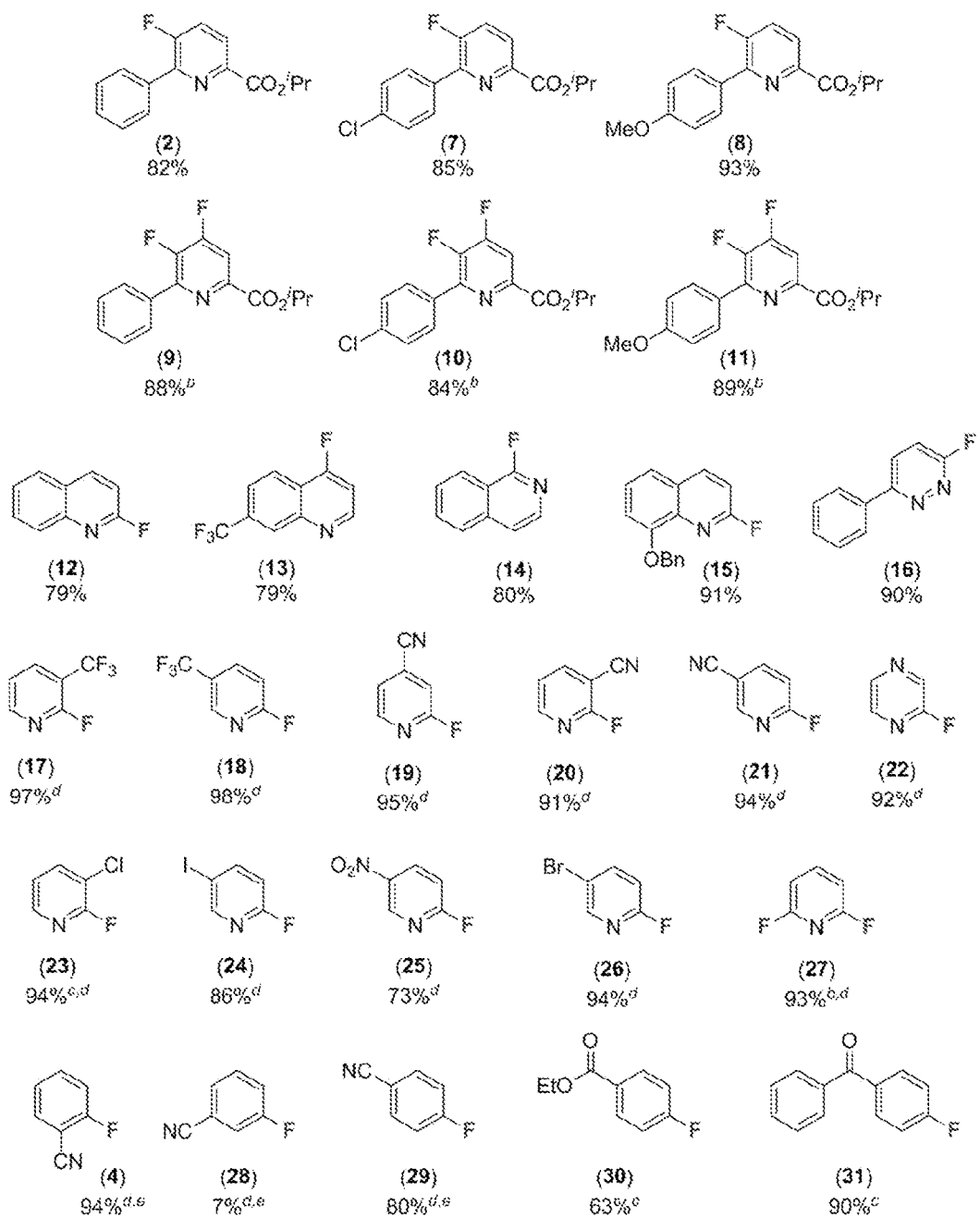
FIG. 3 contains a group of structures exemplifying substrates the disclosed fluorination methods using anhydrous $NMe_4F$. (a) Anhydrous $NMe_4F$ (2 equiv) and substrate (1 equiv) were stirred in DMF at 25° C. for 24 h (b) with 3 equiv of anhydrous $NMe_4F$. (c) The nitroarene was used as the substrate. (d) Yield was determined by $^{19}F$ NMR spectroscopy using 1,3,5-trifluorobenzene as a standard. (e) Reaction was stirred at 80° C. for 24 h.

Time studies for the reactions of 5a-e with anhydrous NMe$_4$F are shown in FIG. 2. In this system, the impact on leaving group on reaction rate is slightly different from that observed for 3a-e, with the order of reactivity being NO$_2$>>Br≈I>Cl>OTf. Interestingly, the initial rate with triflate substrate 5e is actually comparable to that of the aryl bromide; however, the reaction slows dramatically after about 20 min. Overall, the time studies in FIGS. 2 and 3 show that leaving group effects on reaction rates are substrate dependent.

A variety of substrates were tested with the disclosed methods using anhydrous NMe$_4$F. As shown in FIG. 3, a variety of monochloropicolinates and dichloropicolinates reacted to afford the corresponding mono- and difluorinated products 2 and 7-11 in good to excellent isolated yields. Notably, these transformations were all conducted at room temperature over 24 h, and the reactions of dichloropicolinate substrates required only 1.5 equiv of TMAF per chloride.

Chloroquinoline, chloroisoquinoline, and chloropyridazine substrates also underwent room temperature fluorination to form 12-16 in excellent yields. The high yielding synthesis of 8-(benzyloxy)-2-fluoroquinoline (15) is particularly noteworthy, as $^{18}$F-15 has been used for the PET imaging of amyloid plaques. Methoxy, cyano, and trifluoromethyl substituents are compatible with the reaction conditions (products 8, 11, 13, and 17-21). In addition, halide (Cl, Br, and I) and nitro substituents at less activated positions in the molecule are well tolerated even in the presence of excess NMe$_4$F (products 7, 10, and 23-26). Less activated aryl chlorides required higher temperatures to form the desired product in low to excellent yield (products 4, 28, and 29). S$_N$Ar fluorination with NMe$_4$F produced 2- and 4-fluorobenzonitrile (4 and 29) in excellent yields, while 3-fluorobenzonitrile 28 was formed in low yields. This result is consistent with previous reports of halex reactions using anhydrous fluoride showing that substituents in the meta position do not activate the aryl ring for S$_N$Ar reactions (Sun, H.; et al., Angew. Chem. Int. Ed. 2006; 45:2720). While ethyl 4-chlorobenzoate and 4-chlorobenzophenone were not sufficiently activated for the S$_N$Ar fluorination with NMe$_4$F (even at 80° C.), the nitro analogs reacted to afford high yields of the fluorinated products at room temperature (30 and 31).

A series of experiments was performed to evaluate the effect of different solvents on fluorination with NMe$_4$F at room temperature for 24 hours. The results are shown in Table 5.

TABLE 5

Solvent effects on S$_N$Ar reactions

| solvent | solubility | yield |
|---|---|---|
| DMF | partially soluble | 80% |
| MeCN | partially soluble | 0% |
| DMAc | partially soluble | 22% |
| sulfolane | soluble | 30% |
| DMSO | soluble | 28% |
| propylene carbonate | soluble | 0% |

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

NMR spectra were obtained on a Varian MR400 (400.52 MHz for $^1$H; 376.87 MHz for $^{19}$F; 100.71 MHz for $^{13}$C), a Varian vnmrs 500 (500.01 MHz for $^1$H; 125.75 MHz for $^{13}$C; 470.56 MHz for $^{19}$F), a Varian vnmrs 700 (699.76 MHz for $^1$H; 175.95 MHz for $^{13}$C), or a Varian Inova 500 (499.90 MHz for $^1$H; 125.70 MHz for $^{13}$C) spectrometer. $^1$H and $^{13}$C chemical shifts are reported in parts per million (ppm) relative to TMS, with the residual solvent peak used as an internal reference (CDCl$_3$; $^1$H δ 7.26 ppm; $^{13}$C δ 77.16 ppm). $^{19}$F NMR spectra are referenced based on the internal standard 1,3,5-trifluorobenzene, which appears at −108.33 ppm. Multiplicities are reported as follows: singlet (s), doublet (d), triplet (t), quartet (q), multiplet (m), doublet of doublets (dd), doublet of triplets (dt). Coupling constants (J) are reported in Hz. GCMS analysis was performed on a Shimadzu GCMS-QP2010 plus gas chromatograph mass spectrometer. The products were separated on a 30 m length by 0.25 mm id RESTEK XTI-5 column coated with a 0.25 µm film. Helium was employed as the carrier gas, with a constant column flow of 1.5 mL/min. The injector temperature was held constant at 250° C. The GC oven temperature program for low molecular weight compounds was as follows: 32° C. hold 5 min, ramp 15° C./min to 250° C., and hold for 1.5 min. The GC oven temperature program for medium molecular weight compounds was as follows: 60° C., hold for 4 minutes, ramp 15° C./min to 250° C. Unless otherwise noted, the medium molecular weight method was used for GCMS analysis. Melting points were determined with a Thomas Hoover Uni-Melt 6427-H10 Capillary Melting-Point Apparatus and are uncorrected. High-resolution mass spectra were recorded on a Micromass AutoSpec Ultima Magnetic Sector mass spectrometer.

Commercial reagents were used as received unless otherwise noted. Anhydrous tetramethylammonium fluoride was obtained from Sigma Aldrich. Anhydrous N,N-dimethylformamide was obtained from Alfa Aesar. Isopropyl chloroarylpicolinates were prepared using previously described methods (Allen, L. J.; et al., J. Org. Chem. 2014; 79:5827). 2-Cyanophenyl trifluoromethanesulfonate (Qin, L.; et al., Angew. Chem. Int. Ed. 2012; 51:5915), pyridine-2-yl trifluoromethanesulfonate (Xu, X.-H.; et al., Org. Lett. 2012; 14:2544), and 8-(benzyloxy)-2-chloroquinoline (JP2011-153115) were prepared using literature procedures and dried over P$_2$O$_5$ prior to use.

General Procedures for Fluorination Reactions

General Procedure A: Experimental Details for Fluorination Reactions Reported in Table 1.

In a drybox, substrate 1 (0.1 mmol, 1.0 equiv) and anhydrous tetramethylammonium fluoride (NMe$_4$F) were weighed into a 4 mL vial equipped with a micro stirbar. DMF (0.5 mL) was added, and the reaction vial was sealed with a Teflon-lined cap, removed from the drybox, and stirred at the designated temperature for 24 hours. The reaction was then cooled to room temperature, diluted with dichloromethane (2.5 mL), and an internal standard (1,3,5-trifluorobenzene, 100 µL of a 0.5 M solution in toluene) was added. An aliquot was removed for analysis by $^{19}$F NMR spectroscopy.

General Procedure B: Experimental Details for Fluorination Reactions Reported in Table 2.

A solution of anhydrous DMF (2 mL) and deionized water that was sparged with $N_2$ was prepared in a Schlenk flask and sparged with $N_2$ for 15 minutes. The Schlenk tube was then pumped into a drybox. In a drybox, substrate 1 (0.1 mmol, 1.0 equiv) and anhydrous $NMe_4F$ (0.2 mmol, 2.0 equiv) were weighed into a 4 mL equipped with a micro stirbar. The water-DMF solution was then added (0.5 mL), and the reaction vial was sealed with a Teflon-lined cap, removed from the drybox, and stirred at room temperature for 24 hours. The reaction was then diluted with dichloromethane (2.5 mL), and an internal standard (1,3,5-trifluorobenzene, 100 µL of a 0.5 M solution in toluene) was added. An aliquot was removed for analysis by $^{19}$F NMR spectroscopy.

General Procedure C: Experimental Details for Fluorination Reactions Reported in Tables 3 and 4 and FIGS. 1 and 2.

For reactions with anhydrous $NMe_4F$: In a drybox, substrate 3a-e or 5a-e (0.1 mml, 1.0 equiv) and anhydrous $NMe_4F$ (0.2 mmol, 2 equiv) were weighed into a 4 mL vial equipped with a micro stirbar. DMF (0.5 mL) was added, and the reaction vial was sealed with a Teflon-lined cap, removed from the drybox, and stirred at the given temperature for the given time. The reactions were cooled at 0° C., diluted with dichloromethane (2.5 mL), and an internal standard (1,3,5-trifluorobenzene, 100 µL of a 0.5 M solution in toluene) was added. An aliquot was removed for analysis by $^{19}$F NMR spectroscopy.

For reactions with CsF (Comparative): In a drybox, substrate 3a-e or 5a-e (0.1 mmol, 1.0 equiv) and CsF (0.2 mmol, 2 equiv) were weighed into a 4 mL vial equipped with a micro stirbar. DMF (0.5 mL) was added, and the reaction vial was sealed with a Teflon-lined cap, removed from the drybox, and stirred at 140° C. for 24 hours. The reactions were cooled to room temperature, diluted with dichloromethane (2.5 mL), and an internal standard (1,3,5-trifluorobenzene, 100 µL of a 0.5 M solution in toluene) was added. An aliquot was removed for analysis by $^{19}$F NMR spectroscopy.

General Procedure D: Experimental Details for Isolated Yields Reported in FIG. 3.

In a drybox, anhydrous $NMe_4F$ (93 mg, 1 mmol, 2 equiv) and the appropriate aryl chloride or nitroarene substrate (0.5 mmol, 1 equiv) were weighed into a 4 mL vial equipped with a micro stirbar. DMF (2.5 mL) was added, and the vial removed from the drybox and stirred at room temperature for 24 hours. The reaction was then diluted with dichloromethane (15 mL) and transferred to a separatory funnel. The organic layer was washed with water (3×25 mL) and brine (1×25 mL), dried over magnesium sulfate, and concentrated in vacuo. The crude mixture was purified by flash column chromatography on silica gel using gradients of hexanes and either diethyl ether or ethyl acetate as eluent.

General Procedure E: General Experimental Details for NMR Yields Reported in FIG. 3.

In a drybox, anhydrous $NMe_4F$ (18.6 mg, 0.2 mmol, 2 equiv) and the appropriate aryl chloride or nitroarene substrate (0.1 mmol, 1 equiv) were weighed into a 4 mL vial equipped with a micro stirbar. DMF (0.5 mL) was added, and the vial was removed from the drybox and stirred at room temperature unless otherwise noted for 24 hours. The reaction was cooled to room temperature and an internal standard (1,3,5-trifluorobenzene, 100 µL of a 0.5 M solution in toluene) was added. An aliquot was removed for analysis by $^{19}$F NMR spectroscopy and GCMS.

Product Synthesis and Characterization

Isopropyl 5-Fluoro-6-phenylpicolinate (2)

General procedure D was followed using isopropyl 5-chloro-6-phenylpicolinate (1) (138 mg, 0.5 mmol, 1 equiv), providing 2 as a colorless oil (106 mg, 82% yield, $R_f$=0.61 in 70% hexanes/30% $Et_2O$). $^1$H, $^{13}$C, and $^{19}$F experimental data match those reported in the literature (Allen, L. J.; et al., *J Org. Chem.* 2014; 79:5827). $^1$H NMR (500 MHz, $CDCl_3$): δ 8.06 (d, J=7.0 Hz, 3H), 7.56 (dd, J=10.5, 8.5 Hz, 1H), 7.51-7.44 (m, 3H), 5.32 (septet, J=6.5 Hz, 1H), 1.43 (d, J=6.0, 6H). $^{13}$C NMR (175.95 MHz, $CDCl_3$): δ 163.7, 159.8 (d, J=267 Hz), 146.2 (d, J=12.0 Hz), 144.4 (d, J=4.2 Hz), 134.5 (d, J=5.4 Hz), 129.6, 129.0 (d, J=6.2 Hz), 128.4, 125.3 (d, J=5.4 Hz), 124.6 (d, J=21.9 Hz), 69.5, 21.8. $^{19}$F NMR (100 MHz, $CDCl_3$): δ −117.5 (d, 2.6 Hz). IR ($cm^{-1}$): 1734, 1712, 1463, 1438, 1357, 1312, 1285, 1213, 1101, 1052, 795, 725, 692. HRMS $ESI^+$ (m/z): $[M+H]^+$ calcd for $C_{15}H_{15}FNO_2$ 260.1081; found 260.1080. The yield (82%) represents an average of two runs (82% (above) and 81%).

Isopropyl 5-Fluoro-6-(p-chlorophenyl)picolinate (7)

General procedure D was followed using isopropyl 5-chloro-6-(p-chlorophenyl)picolinate (122 mg, 0.5 mmol, 1 equiv), providing 7 as a white solid (122 mg, 83% yield, $R_f$=0.59 in 70% hexanes/30% $Et_2O$, mp=73-76° C.). $^1$H, $^{13}$C, and $^{19}$F experimental data match those reported in the literature (Ryan, S. J.; et al., *Org. Lett.* 2015; 17:1866). $^1$H NMR (500 MHz, $CDCl_3$): δ 8.07 (dd, J=8.5, 3.5 Hz, 1H), 8.03 (d, J=8.0 Hz, 2H), 7.57 (dd, J=10.5, 8.5 Hz, 1H), 7.47 (d, J=8.5 Hz, 2H), 5.31 (septet, J=6.0 Hz, 1H), 1.43 (d, J=6.5 Hz, 6H). $^{13}$C NMR (175.95 MHz, $CDCl_3$): δ 163.5, 159.7 (d, J=267 Hz), 144.8 (d, J=2.6 Hz), 144.4 (d, J=4.2 Hz), 135.7, 132.9 (d, J=5.5 Hz), 130.3 (d, J=6.7 Hz), 128.6, 125.6 (d, J=5.5 Hz), 124.8 (d, J=21.1 Hz), 69.6, 21.8. $^{19}$F NMR (100 MHz, $CDCl_3$): δ −117.1 (s). IR ($cm^{-1}$): 1726, 1597, 1452, 1408, 1386, 1286, 1218, 1142, 1110, 1085, 1047, 866, 839. HRMS $ESI^+$ (m/z): $[M+H]^+$ calcd for $C_{15}H_{14}ClFNO_2$ 294.0692; found 294.0689. The yield (85%) represents an average of two runs (83% (above) and 87%).

Isopropyl 5-Fluoro-6-(p-methoxyphenyl)picolinate (8)

General procedure D was followed using isopropyl 5-chloro-6-(p-methoxyphenyl)picolinate (153 mg, 0.5 mmol, 1 equiv), providing 8 as a white solid (138 mg, 96% yield, $R_f$=0.38 in 70% hexanes/30% $Et_2O$, mp=46-48° C.). $^1$H, $^{13}$C, and $^{19}$F experimental data match those reported in the literature (Id.). $^1$H NMR (500 MHz, $CDCl_3$): δ 8.05 (d, J=7.5 Hz, 2H), 7.98 (dd, J=8.0, 3.5 Hz, 1H), 7.52 (dd, J=10.5, 8.5 Hz, 1H), 7.01 (d, J=8.5 Hz, 2H), 5.30 (septet, J=6.5 Hz, 1H), 3.86 (s, 3H), 1.42 (d, J=6.5 Hz, 6H). $^{13}$C NMR (175.95 MHz, CDCl$_3$): δ 163.8, 160.7, 159.5 (d, J=267 Hz), 145.8 (d, J=10.9 Hz), 144.2 (d, J=4.8 Hz), 130.4 (d, J=6.7 Hz), 127.1 (d, J=6.2 Hz), 124.5 (d, J=5.5 Hz), 124.4 (d, J=21.6 Hz), 113.8, 69.4, 55.2, 21.8. $^{19}$F NMR (100 MHz, CDCl$_3$): δ −117.7 (s). IR (cm$^{-1}$): 1703, 1609, 1453, 1359, 1310, 1256, 1213, 1183, 1136, 1101, 1050, 1021, 754. HRMS ESI$^+$ (m/z): [M+H]$^+$ calcd for C$_{16}$H$_{17}$FNO$_3$ 290.1187; found 290.1185. The yield (93%) represents an average of two runs (96% (above) and 90%).

Isopropyl 4,5-Difluoro-6-phenylpicolinate (9)

General procedure D was followed using isopropyl 4,5-dichloro-6-phenylpicolinate (155 mg, 0.5 mmol, 1 equiv) and anhydrous NMe$_4$F (140 mg, 1.5 mmol, 3 equiv), providing 9 as a colorless oil (121 mg, 87% yield, R$_f$=0.64 in 70% hexanes/30% Et$_2$O). $^1$H, $^{13}$C, and $^{19}$F experimental data match those reported in the literature (Allen, L. J.; et al., J. Org. Chem. 2014; 79:5827). $^1$H NMR (500 MHz, CDCl$_3$): δ 8.03 (d, J=7.5 Hz, 2H), 7.88 (dd, J=9.0, 5.0 Hz, 1H), 7.50-7.45 (m, 3H), 5.30 (septet, J=6.5 Hz), 1.42 (d, J=6.5 Hz, 6H). $^{13}$C NMR (175.95 MHz, CDCl$_3$): δ 162.8 (d, J=2.8 Hz), 157.4 (d, J=13.0 Hz), 155.9 (d, J=13.0 Hz), 148.4 (d, J=7.6 Hz), 147.2 (dd, J=270, 10.2 Hz), 145.4 (t, J=6.7 Hz), 133.8 (dd, J=5.3, 3.3 Hz), 130.1, 129.0 (d, J=6.2 Hz), 128.6 (d, J=15.0 Hz), 113.5 (d, J=16.3 Hz), 70.0, 21.7. $^{19}$F NMR (100 MHz, CDCl$_3$): δ −144.8 (m, 1F), −125.2 (m, 1F). IR (cm$^{-1}$): 1744, 1714, 1605, 1471, 1435, 1416, 1371, 1226, 1135, 1094, 974, 879, 786, 737, 714, 691. HRMS ESI$^+$ (m/z): [M+H]$^+$ calcd for C$_{15}$H$_{14}$F$_2$NO$_2$ 278.0987; found 278.0986. The yield (88%) represents an average of two runs (87% (above) and 88%).

Isopropyl 4,5-Difluoro-6-(p-chlorophenyl)picolinate (10)

General procedure D was followed using isopropyl 4,5-dichloro-6-(p-chlorophenyl)picolinate (172 mg, 0.5 mmol, 1 equiv) and anhydrous NMe$_4$F (140 mg, 1.5 mmol, 3 equiv), providing 10 as a white solid (138 mg, 89% yield, R$_f$=0.69 in 70% hexanes/30% Et$_2$O, mp=74-76° C.). $^1$H, $^{13}$C, and $^{19}$F experimental data match those reported in the literature (Id.). $^1$H NMR (500 MHz, CDCl$_3$): δ 7.98 (d, J=8.0 Hz, 2H), 7.87 (dd, J=9.5, 5.5 Hz, 1H), 7.44 (d, J=9.0 Hz, 2H), 5.28 (septet, J=6.5 Hz, 1H), 1.41 (d, J=6.0 Hz, 6H). $^{13}$C NMR (175.95 MHz, CDCl$_3$): δ 162.6 (d, J=3.3 Hz), 157.5 (d, J=12.8 Hz), 156.0 (d, J=12.1 Hz), 147.2 (dd, J=269, 10.9 Hz), 147.0 (d, J=7.6 Hz), 145.4 (t, J=6.2 Hz), 136.4, 132.1 (dd, J=23.0, 3.5 Hz), 130.2 (d, J=6.8 Hz), 128.8, 113.7 (d, J=15.6 Hz), 70.1, 21.7. $^{19}$F NMR (100 MHz, CDCl$_3$): β −144.3 (m, 1F), −124.7 (m, 1F). IR (cm$^{-1}$): 1715, 1594, 1496, 1463, 1419, 1394, 1345, 1243, 1217, 1174, 1090, 974, 909, 878, 829, 789, 753. HRMS ESI$^+$ (m/z): [M+H]$^+$ calcd for C$_{15}$H$_{13}$ClF$_2$NO$_2$ 312.0597; found 312.0597. The yield (84%) represents an average of two runs (89% (above) and 79%).

Isopropyl 4,5-Difluoro-6-(p-methoxyphenyl)picolinate (11)

General procedure D was followed using isopropyl 4,5-dichloro-6-(p-methoxyphenyl)picolinate (170 mg, 0.5 mmol, 1 equiv) and anhydrous NMe$_4$F (140 mg, 1.5 mmol, 3 equiv), providing 11 as a white solid (136 mg, 89% yield, R$_f$=0.61 in 70% hexanes/30% Et$_2$O, mp=37-38° C.). $^1$H, $^{13}$C, and $^{19}$F experimental data match those reported in the literature (Id.). $^1$H NMR (500 MHz, CDCl$_3$): δ 8.04 (d, J=8.5 Hz, 2H), 7.81 (dd, J=9.5, 5.0 Hz, 1H), 7.00 (d, J=8.5 Hz, 2H), 5.29 (septet, J=6.0 Hz, 1H), 3.05 (s, 3H), 1.41 (d, J=6.0 Hz, 6H). $^{13}$C NMR (175.95 MHz, CDCl$_3$): δ 162.9 (d, J=2.6 Hz), 161.1, 155.9 (dd, J=264, 12.1 Hz), 148.0 (d, J=7.4 Hz), 146.9 (dd, J=276, 10.4 Hz), 145.1 (t, J=6.9 Hz), 130.5 (d, J=6.2 Hz), 126.4 (d, J=5.4 Hz), 113.9, 112.8 (d, J=16.4 Hz), 69.9, 55.3, 21.7. $^{19}$F NMR (100 MHz, CDCl$_3$): δ −145.2 (d, J=4.7 Hz, 1F), −125.7 (m, 1F). IR (cm$^{-1}$): 1707, 1600, 1586, 1518, 1461, 1409, 1372, 1258, 1238, 1183, 1137, 1089, 1025, 971, 879, 787, 760. HRMS ESI$^+$ (m/z): [M+H]$^+$ calcd for C$_{16}$H$_{16}$F$_2$NO$_3$ 308.1093; found 308.1091. The yield (89%) represents an average of two runs (89% (above) and 88%).

2-Fluoroquinoline (12)

General procedure D was followed using 2-chloroquinoline (82 mg, 0.5 mmol, 1 equiv), providing 12 as a colorless oil (56 mg, 77% yield, R$_f$=0.51 in 70% hexanes/30% Et$_2$O). $^1$H, $^{13}$C, and $^{19}$F experimental data match those reported in the literature (Id.). $^1$H NMR (500 MHz, CDCl$_3$): δ 8.22 (t, J=8.5 Hz, 1H), 7.95 (d, J=8.5 Hz, 1H), 7.83 (d, J=8.0 Hz, 1H), 7.72 (t, J=8.0 Hz, 1H), 7.52 (t, J=8.0 Hz, 1H), 7.07 (dd, J=9.0, 2.5 Hz, 1H). $^{13}$C NMR (175.95 MHz, CDCl$_3$): δ 161.7 (d, J=242 Hz), 145.7 (d, J=17.1 Hz), 141.9 (d, J=10.2 Hz), 130.5, 128.0, 127.5, 126.8, 126.1 (d, J=2.6 Hz), 110.1 (d, J=42.2 Hz). $^{19}$F NMR (100 MHz, CDCl$_3$): δ −61.6 (s). IR (cm$^{-1}$): 1620, 1601, 1579, 1507, 1472, 1428, 1309, 1271, 1251, 1230, 1205, 1107, 967, 815, 777, 752, 706. HRMS ESI$^+$ (m/z): [M+H]$^+$ calcd for C$_9$H$_7$FN 148.0557; found 148.0555. The yield (79%) represents an average of two runs (77% (above) and 80%).

4-Fluoro-7-(trifluoromethyl)quinoline (13)

General procedure D was followed using 4-chloro-7-(trifluoromethyl)quinoline (116 mg, 0.5 mmol, 1 equiv), providing 13 as a white solid (88 mg, 82% yield, R$_f$=0.38 in 70% hexanes/30% Et$_2$O, mp=84-86° C.). $^1$H, $^{13}$C, and $^{19}$F experimental data match those reported in the literature (Id.). $^1$H NMR (500 MHz, CDCl$_3$): δ 8.94 (dd, J=8.0, 5.0 Hz, 1H), 8.40 (s, 1H), 8.19 (d, J 8.5 Hz, 1H), 7.75 (d, J=9.0 Hz, 1H), 7.19 (dd, J=9.0, 4.5 Hz, 1H). $^{13}$C NMR (175.95 MHz, CDCl$_3$): δ 164.1 (d, J=270 Hz), 152.9 (d, J=8.3 Hz), 149.3 (d, J=4.0 Hz), 132.2 (q, J=33.2 Hz), 127.0 (quintet, J=4.2 Hz), 125.9, 124.3, 122.8, 122.5 (t, J=1.4 Hz), 122.0 (d, J=4.7 Hz), 121.1 (t, J=19.7 Hz), 107.3 (d, J=14.2 Hz). $^{19}$F NMR (100 MHz, CDCl$_3$): δ −111.5 (t, J=1.4 Hz, 1F), −63.0 (s, 3F). IR (cm$^{-1}$): 1616, 1559, 1507, 1456, 1326, 1297, 1193, 1149, 1110, 1058, 905, 833. HRMS ESI$^+$ (m/z): [M+H]$^+$ calcd for C$_{10}$H$_6$F$_4$N 216.0431; found 216.0430. The yield (79%) represents an average of two runs (82% (above) and 75%).

1-Fluoroisoquinoline (14)

General procedure D was followed using 1-chloroquinoline (82 mg, 0.5 mmol, 1 equiv), providing 14 as a colorless oil (59 mg, 80% yield, 0.53 in 70% hexanes/30% Et$_2$O). $^1$H, $^{13}$C, and $^{19}$F experimental data match those reported in the literature (Ryan, S. J.; et al., Org. Lett. 2015:17:1866). $^1$H NMR (500 MHz, CDCl$_3$): δ 8.12 (d, J=8.0 Hz, 1H), 8.02 (d, J=6.0 Hz, 1H), 7.82 (d, J=8.5 Hz, 1H), 7.72 (t, J=7.5 Hz, 1H), 7.61 (t, J=8.0 Hz, 1H), 7.49 (d, J=6.0 Hz, 1H). $^{13}$C NMR (175.95 MHz, CDCl$_3$): δ 160.6 (d, J=247 Hz), 139.6 (d, J=5.5 Hz), 139.2 (d, J=16.4 Hz), 131.4, 127.8, 126.3 (d, J=3.3 Hz), 123.0, 119.3 (d, J=5.4 Hz), 117.7 (d, J=32.7 Hz). $^{19}$F NMR (100 MHz, CDCl$_3$): δ −71.2 (s). IR (cm$^{-1}$): 1637, 1591, 1573, 1497, 1344, 1269, 1051, 819, 748, 720, 658. HRMS ESI⁺ (m/z): [M+H]⁺ calcd for C₉H₇FN 148.0557; found 148.0555. The yield (78%) represents an average of two runs (80% (above) and 76%).

8-(Benzyloxy)-2-fluoroquinoline (15)

General procedure D was followed using 8-(benzyloxy)-2-chloroquinoline (134.5 mg, 0.1 mmol, 1 equiv), providing 15 as a white solid (120 mg, 95% yield, $R_f$=0.38 in 70% hexanes/30% Et₂O, mp=67-69° C.). ¹H and ¹⁹F experimental data match those reported in the literature (Hicken, E. J.; et al., ACS Med. Chem. Lett. 2014; 5:78; WO2014/00730). ¹H NMR (500 MHz, CDCl₃): δ 8.17 (t, J=8.5 Hz, 1H), 7.52 (d, J=7.5 Hz, 2H), 7.36 (q, J=7.5 Hz, 4H), 7.29 (q, J=7.5 Hz, 1H), 7.08 (dd, J=7.5, 3 Hz, 2H), 5.40 (s, 2H). ¹³C NMR (125.75 MHz, CDCl₃): δ 161.5 (d, J=242 Hz), 153.4, 142.0 (d, J=9.5 Hz), 138.7, 137.6 (d, J=15.3 Hz), 136.8, 128.6, 128.0 (d, J=1.9 Hz), 127.0, 126.9, 126.1 (d, J=2.9 Hz), 119.6, 111.6, 110.6 (d, J=42.9 Hz), 70.7. ¹⁹F NMR (100 MHz, CDCl₃): δ −61.07 (t, J=1.5 Hz, 1H). IR (cm⁻¹): 1600, 1507, 1475, 1426, 1378, 1341, 1260, 1239, 1087, 981, 827, 754, 730, 706, 693. HRMS ESI⁺ (m/z): [M+H]⁺ calcd for C₁₆H₁₃FNO, 254.0976; found 254.0975. The yield (91%) represents an average of two runs (95% (above) and 86%).

3-Fluoro-6-phenyl-pyridazine (16)

General procedure D was followed using 3-chloro-6-phenyl-pyridzaine (95 mg, 0.5 mmol, 1 equiv), providing 16 as a white solid (79 mg, 91% yield, $R_f$=0.38 in 70% hexanes/30% Et₂O, mp=129-131° C.). ¹H NMR (500 MHz, CDCl₃): δ 8.01-7.98 (m, 3H), 7.53-7.49 (m, 3H), 7.29 (dd, J=9.5, 2.0 Hz, 1H). ¹³C NMR (175.95 MHz, CDCl₃): δ 166.7 (d, J=245 Hz), 159.2 (d, J=3.5 Hz), 135.1 (d, J=2.1 Hz), 130.2, 129.5 (d, J=7.6 Hz), 129.0, 127.0, 116.1 (d, J=33.4 Hz). ¹⁹F NMR (100 MHz, CDCl₃): −84.8 (d, J=1.5 Hz). IR (cm⁻¹): 1584, 1556, 1450, 1427, 1278, 1108, 852, 778, 739. HRMS ESI⁺ (m/z): [M+H]⁺ calcd for C₁₀H₇FN₂ 175.0666; found 175.0663. The yield (90%) represents an average of two runs (91% (above) and 88%).

2-Fluoro-3-(trifluoromethyl)pyridine (17)

General procedure E was followed using 2-chloro-3-(trifluoromethyl)pyridine (18.1 mg, 0.1 mmol, 1 equiv), providing 17 in 100% yield as determined by ¹⁹F NMR spectroscopic analysis of the crude reaction mixture. The product showed a ¹⁹F NMR signals at −63.42 (3F) and −68.06 (1F) ppm in DCM (lit. −60.62 (3F), −63.01 (1F) ppm in DMSO) (Sun, H.; et al. Angew. Chem. Int. Ed. 2006; 45:270). The identity of the product was further confirmed by GCMS analysis, where the product peak was observed at 6.07 min using the low molecular weight method. The yield (97%) represents an average of two runs (100% (above) and 97%).

2-Fluoro-5-(trifluoromethyl)pyridine (18)

General procedure E was followed using 2-chloro-5-(trifluoromethyl)pyridine (18.1 mg, 0.1 mmol, 1 equiv), providing 18 in 95% yield as determined by ¹⁹F NMR spectroscopic analysis of the crude reaction mixture. The product showed ¹⁹F NMR signals at −62.68 (3F) and −63.51 (1F) ppm in DCM (lit. −60.62 (3F), −63.01 (1F) ppm in DMSO) (Id.). The identity of the product was further confirmed by GCMS analysis, where the product peak was observed at 4.48 min using the low molecular weight method. The yield (98%) represents an average of two runs (95% (above) and 100%).

2-Fluoro-4-cyanopyridine (19)

General procedure E was followed using 2-chloro-4-cyanopyridine (13.8 mg, 0.1 mmol, 1 equiv), providing 19 in 100% yield as determined by ¹⁹F NMR spectroscopic analysis of the crude reaction mixture. The ¹⁹F NMR spectral data matched that of an authentic sample (Synthonix, s, −64.94 ppm). The identity of the product was further confirmed by GCMS analysis, where the product peak was observed at 6.13 min. The yield (95%) represents an average of two runs (100% (above) and 89%).

2-Fluoro-3-cyanopyridine (20)

General procedure E was followed using 2-chloro-3-cyanopyridine (13.8 mg, 0.1 mmol, 1 equiv), providing 20 in 93% yield as determined by ¹⁹F NMR spectroscopic analysis of the crude reaction mixture. The product showed a ¹⁹F NMR signal at −62.66 ppm in DCM (lit. −60.0 ppm in CDCl₃) (Umemoto, T.; et al., J. Org. Chem. 1989; 54:1726). The identity of the product was further confirmed by GCMS analysis, where the product peak was observed at 7.55 min. The yield (91%) represents an average of two runs (93% (above) and 88%).

2-Fluoro-5-cyanopyridine (21)

General procedure E was followed using 2-chloro-5-cyanopyridine (13.8 mg, 0.1 mmol, 1 equiv), providing 21 in 87% yield as determined by ¹⁹F NMR spectroscopic analysis of the crude reaction mixture. The ¹⁹F NMR spectral data matched that of an authentic sample (Matrix Scientific, s, −59.41 ppm). The identity of the product was further confirmed by GCMS analysis, where the product peak was observed at 6.95 min. The yield (94%) represents an average of two runs (87% (above) and 100%).

2-Fluoropyrazine (22)

General procedure E was followed using 2-chloropyrazine (11.4 mg, 0.1 mmol, 1 equiv), providing 22 in 99% yield as determined by ¹⁹F NMR spectroscopic analysis of the crude reaction mixture. The product showed a ¹⁹F NMR signal at −81.00 ppm in DCM (lit. −80.4 ppm in DMSO) (Sun, H.; et al. Angew. Chem. Int. Ed. 2006; 45:2720). The identity of the product was further confirmed by GCMS analysis, where the product peak was observed at 3.93 min using the low molecular weight method. The yield (92%) represents an average of two runs (99% (above) and 84%).

2-Fluoro-3-chloropyridine (23)

General procedure E was followed using 2-nitro-3-chloropyridine (15.8 mg, 0.1 mmol, 1 equiv), providing 23 in 94% yield as determined by ¹⁹F NMR spectroscopic analysis of the crude reaction mixture. The product showed a ¹⁹F NMR signal at −72.54 ppm in DCM (lit. −73.03 ppm in DMSO) (Id.). The identity of the product was further confirmed by GCMS analysis, where the product peak was observed at 5.48 min. The yield (94%) represents an average of two runs ([94% (above) and 94%).

2-Fluoro-5-iodopyridine (24)

General procedure E was followed using 2-chloro-5-iodopyridine (23.9 mg, 0.1 mmol, 1 equiv), providing 24 in 85% yield as determined by $^{19}$F NMR spectroscopic analysis of the crude reaction mixture. The $^{19}$F NMR spectral data matched that of an authentic sample (Sigma Aldrich, m, −71.28 ppm). The identity of the product was further confirmed by GCMS analysis, where the product peak was observed at 8.28 min. The yield (86%) represents an average of two runs (85% (above) and 87%).

2-Fluoro-5-nitropyridine (25)

General procedure E was followed using 2-chloro-5-nitropyridine (15.8 mg, 0.1 mmol, 1 equiv), providing 25 in 70% yield as determined by $^{19}$F NMR spectroscopic analysis of the crude reaction mixture. The $^{19}$F NMR spectral data matched that of an authentic sample (Oakwood Chemicals, s, −59.14 ppm). The identity of the product was further confirmed by GCMS analysis, where the product peak was observed at 8.08 min. The yield (73%) represents an average of two runs (70% (above) and 76%).

2-Fluoro-5-bromopyridine (26)

General procedure E was followed using 2-chloro-5-bromopyridine (19.1 mg, 0.1 mmol, 1 equiv), providing 26 in 100% yield as determined by $^{19}$F NMR spectroscopic analysis of the crude reaction mixture. The $^{19}$F NMR spectral data matched that of an authentic sample (Oakwood Products, s, −71.69 ppm). The identity of the product was further confirmed by GCMS analysis, where the product peak was observed at 6.54 min. The yield (94%) represents an average of two runs (100% (above) and 88%).

2, 6-Difluoropyridine (27)

General procedure E was followed using 2,6-dichloropyridine (14.7 mg, 0.1 mmol, 1 equiv) and anhydrous NMe$_4$F (28 mg, 0.3 mmol, 3 equiv), providing 27 in 91% yield as determined by $^{19}$F NMR spectroscopic analysis of the crude reaction mixture. The $^{19}$F NMR spectral data matched that of an authentic sample (Alfa Aesar, m, −68.91 ppm). The identity of the product was further confirmed by GCMS analysis, where the product peak was observed at 4.87 min using low molecular weight method. The yield (93%) represents an average of two runs (91% (above) and 95%).

2-Fluorobenzonitrile (4)

General procedure E was followed using 2-chlorobenzonitrile (13.7 mg, 0.1 mmol, 1 equiv) at 80° C., providing 4 in 98% yield as determined by $^{19}$F NMR spectroscopic analysis of the crude reaction mixture. The $^{19}$F NMR spectral data matched that of an authentic sample (Ark Pharm, m, −108.02 ppm). The identity of the product was further confirmed by GCMS analysis, where the product peak was observed at 7.10 min. The yield (94%) represents an average of three runs (99% (above), 83% and 100%).

3-Fluorobenzonitrile (28)

General procedure E was followed using 3-benzonitrile (13.7 mg, 0.1 mmol, 1 equiv) at 80° C., providing 28 in 6% yield as determined by $^{19}$F NMR spectroscopic analysis of the crude reaction mixture. The $^{19}$F NMR spectral data matched that of an authentic sample (Oakwood Chemicals, m, −111.18 ppm). The identity of the product was further confirmed by GCMS analysis, where the product peak was observed at 6.35 min. The yield (7%) represents an average of two runs (6% (above) and 7%).

4-Fluorobenzonitrile (29)

General procedure E was followed using 4-chlorobenzonitrile (13.7 mg, 0.1 mmol, 1 equiv) at 80° C., providing 29 in 79% yield as determined by $^{19}$F NMR spectroscopic analysis of the crude reaction mixture. The $^{19}$F NMR spectral data matched that of an authentic sample (Oakwood Chemicals, m, −103.89 ppm). The identity of the product was further confirmed by GCMS analysis, where the product peak was observed at 6.72 min. The yield (80%) represents an average of two runs (79% (above) and 81%).

Ethyl 4-Fluorobenzoate (30)

General procedure D was followed using ethyl 4-nitrobenzoate (98 mg, 0.5 mmol, 1 equiv), providing 30 as a colorless oil (51 mg, 61% yield, R$_f$=0.58 in 90% hexanes/10% EtOAc). $^1$H, $^{13}$C, and $^{19}$F experimental data match those reported in the literature (Ryan, S. J.; et al. Org. Lett. 2015; 17:1866). $^1$H NMR (500 MHz, CDCl$_3$): δ 8.04 (dt, J 5.5, 2.0 Hz, 2H), 7.08 (t, J=8.5 Hz, 2H), 4.36 (q, J=7.0 Hz, 2H), 1.37 (t, J=7.0 Hz, 3H). $^{13}$C NMR (175.95 MHz, CDCl$_3$): δ 166.3 (d, J=253 Hz), 165.6, 132.0 (d, J 9.5 Hz), 126.7 (d, J=2.6 Hz), 115.4 (d, J=21.8 Hz), 61.0, 14.2. $^{19}$F NMR (100 MHz, CDCl$_3$): δ −160.1 (m). IR (cm$^{-1}$): 1715, 1601, 1507, 1236, 1153, 1105, 1089, 1015, 853, 765, 687. HRMS ESI$^+$ (m/z): [M]$^+$ calcd for C$_9$H$_9$FO$_2$ 168.0587; found 168.0584. The yield (63%) represents an average of two runs (61% (above) and 65%).

4-Fluorobenzophenone (31)

General procedure D was followed using 4-nitrobenzophenone (114 mg, 0.5 mmol, 1 equiv), providing 31 as a white solid (89 mg, 89% yield, R$_f$=0.54 in 90% hexanes/10% EtOAc, mp=47-48° C.). $^1$H, $^{13}$C, and $^{19}$F experimental data match those reported in the literature (Id.). $^1$H NMR (500 MHz, CDCl$_3$): δ 7.85-7.82 (m, 2H), 7.76 (d, J=7.5 Hz, 2H), 7.58 (t, J=7.5 Hz, 1H), 7.47 (t, J=7.5 Hz, 2H), 7.14 (t, J=8.5 Hz, 2H). $^{13}$C NMR (175.95 MHz, CDCl$_3$): δ 195.2, 166.0 (d, J=254 Hz), 137.4, 133.7 (d, J=2.6 Hz), 132.6 (d, J=9.5 Hz), 129.8, 128.3, 115.4 (d, J 22.5 Hz). $^{19}$F NMR (100 MHz, CDCl$_3$): δ −105.9 (m). IR (cm$^{-1}$): 1645, 1594, 1500, 1297, 1279, 1223, 1148, 939, 924, 849, 793, 733, 678. HRMS ESI$^+$ (m/z): [M+H]$^+$ calcd for C$_{13}$H$_{10}$FO 201.0710; found 201.0708. The yield (90%) represents an average of two runs (89% (above) and 90%).

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of preparing a fluorinated aryl or heteroaryl substrate, comprising: combining tetramethylammonium fluoride and an aryl or heteroaryl substrate substituted with at least one chloro, bromo, iodo, nitro, or sulfonate group, at from 0° C. to 55° C.

2. The method of claim 1, wherein the tetramethylammonium fluoride and the aryl or heteroaryl substrate are combined at from 15° C. to 50° C.

3. The method of claim 1, wherein the tetramethylammonium fluoride and the aryl or heteroaryl substrate are combined at from 20° C. to 40° C.

4. The method of claim 1, wherein the tetramethylammonium fluoride and the aryl or heteroaryl substrate are combined at room temperature.

5. The method of claim 1, wherein the tetramethylammonium fluoride and the aryl or heteroaryl substrate are combined for from 1 minute to 24 hours.

6. The method of claim 1, wherein the tetramethylammonium fluoride and the aryl or heteroaryl substrate are combined for from 1 minute to 3.5 hours.

7. The method of claim 1, wherein the tetramethylammonium fluoride and the aryl or heteroaryl substrate are combined in the presence of a solvent.

8. The method of claim 7, wherein the solvent is a polar aprotic solvent.

9. The method of claim 7, wherein the solvent is one or more of dimethylformamide, dimethylacetamide, sulfolane, dimethylsulfoxide, N-methylpyrrolidone, tetrahydrofuran, benzonitrile, or deuterated analogs thereof.

10. The method of claim 7, wherein the tetramethylammonium fluoride and the aryl or heteroaryl substrate are combined at about room temperature and the solvent is dimethylformamide.

11. The method of claim 1, wherein from 0.5 to 10 equivalents of the tetramethylammonium fluoride is used per equivalent of the aryl or heteroaryl substrate.

12. The method of claim 1, wherein from 1 to 2 equivalents of the tetramethylammonium fluoride is used per equivalent of the aryl or heteroaryl substrate.

13. The method of claim 1, wherein the tetramethylammonium fluoride is anhydrous.

14. The method of claim 1, wherein the tetramethylammonium fluoride and the aryl or heteroaryl substrate are combined in the presence of up to 2 equivalents of water per equivalent of the tetramethylammonium fluoride.

15. The method of claim 1, wherein the tetramethylammonium fluoride is combined with the heteroaryl substrate and the heteroaryl substrate has Formula I-A or I-B:

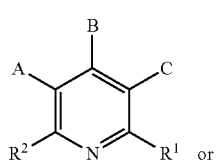

I-A

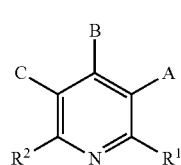

I-B wherein
A is Cl, Br, I, $NO_2$, or $SO_3R^3$;
B is H, Cl, Br, I, $NO_2$, or $SO_3R_3$;
C is H, Cl, Br, I, $NO_2$, or $SO_3R^3$;
$R^1$ is H, CN, $SO_2R^3$, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, substituted or unsubstituted heteroaryl; and the resulting fluorinated product has Formula II-A or II-B

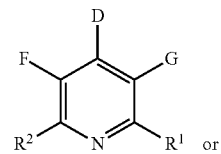

II-A

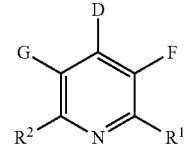

II-B wherein D is B or F; and G is C or F.

16. The method of claim 1, wherein the tetramethylammonium fluoride is combined with the heteroaryl substrate and the heteroaryl substrate has Formula III-A:

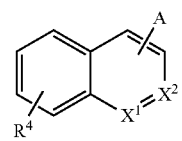

III-A wherein
one of $X^1$ and $X^2$ is N and the other is CH or C-A;
A is Cl, Br, I, $NO_2$, or $SO_3R^3$;
$R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^4$ is H, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, CN, $SO_2R^3$, $OR^3$, $CO_2R^3$, substituted or unsubstituted aryl, substituted or unsubstituted heteroaryl;

And the fluorinated product has Formula III-B

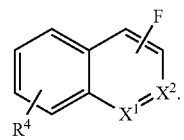

III-B

17. The method of claim 1, wherein the tetramethylammonium fluoride is combined with the heteroaryl substrate and the heteroaryl substrate has Formula IV-A:

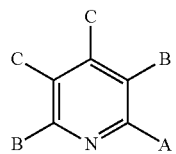

IV-A wherein

A is Cl, Br, I, NO$_2$, or SO$_3$R$^3$;

each B is independent of the other H, Cl, Br, I, NO$_2$, SO$_3$R$^3$, SO$_2$R$^3$, CN, R$^3$, COR$^3$, or CO$_2$R$^3$;

each C is independent of the other H, Cl, Br, I, NO$_2$, SO$_3$R$^3$, SO$_2$R$^3$, CN, R$^3$, COR$^3$, or CO$_2$R$^3$;

R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl;

and the resulting fluorinated product has Formula IV-B

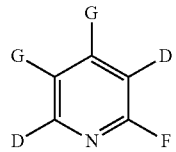

IV-B wherein each D is independently selected from B or F; and each G is independently selected from C or F.

18. The method of claim 1, wherein the tetramethylammonium fluoride is combined with the aryl substrate and the aryl substrate has Formula V-A:

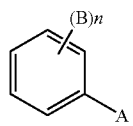

V-A wherein

A is Cl, Br, I, or SO$_3$R$^3$;

n is 0-5;

each B is, independent of any other, Cl, Br, I, CN, SO$_2$R$^3$, R$^3$, COR$^3$, or CO$_2$R$^3$;

R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl;

and the resulting fluorinated product has Formula V-B

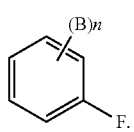

V-B

19. The method of claim 1, wherein the tetramethylammonium fluoride is combined with the heteroaryl substrate and the aryl substrate has Formula VI-A, VI-B, or VI-C:

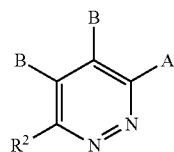

VI-A

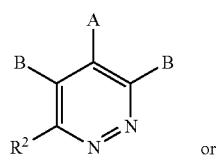

VI-B or

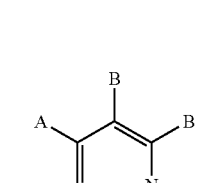

VI-C wherein

A is Cl, Br, I, NO$_2$, or SO$_3$R$^3$;

each B is independent of the other H, Cl, Br, I, CN, NO$_2$, SO$_2$R$^3$, SO$_2$R$^3$, R$^3$, COR$^3$, or CO$_2$R$^3$;

R$^2$ is H, substituted or unsubstituted aryl, substituted or unsubstituted heteroaryl;

R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl;

and the resulting fluorinated product can have Formula VI-D, VI-E, or VI-F:

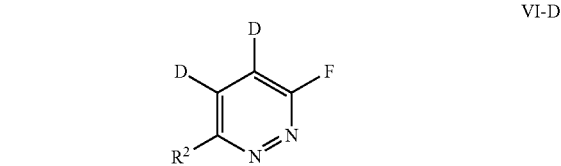

VI-D

VI-E or

VI-F

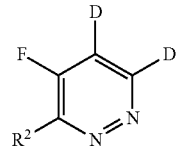

wherein each D is independently selected from B or F.

20. The method of claim 1, wherein the tetramethylammonium fluoride is combined with the heteroaryl substrate and the heteroaryl substrate has Formula VII-A:

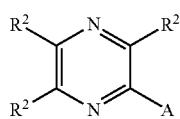

VII-A wherein
A is Cl, Br, I, NO$_2$, or SO$_3$R$^3$;
each R$^2$ is independent of one another H, halide, substituted or unsubstituted aryl, substituted or unsubstituted heteroaryl; and
R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl;
and the resulting fluorinated product can have Formula VII-B

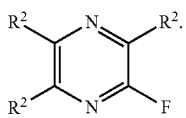

VII-B

21. The method of claim 1, wherein the tetramethylammonium fluoride is combined with the heteroaryl substrate and the heteroaryl substrate has Formula VIII-A:

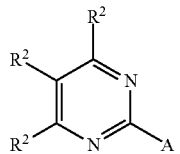

VIII-A wherein
A is Cl, Br, I, NO$_2$, or SO$_3$R$^3$;
each R$^2$ is independent of one another H, substituted or unsubstituted aryl, substituted or unsubstituted heteroaryl; and
R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl.

22. A method of preparing a fluorinated heteroaryl substrate, comprising: combining tetramethylammonium fluoride and a heteroaryl substrate at from 0° C. to 80° C., wherein the heteroaryl substrate has Formula I-A or I-B:

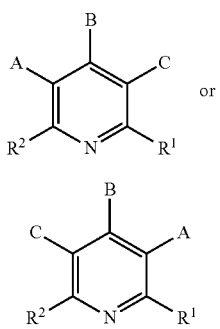

wherein
A is Cl, Br, I, NO$_2$, or SO$_3$R$^3$;
B is H, Cl, Br, I, NO$_2$, or SO$_3$R$^3$;
C is H, Cl, Br, I, NO$_2$, or SO$_3$R$^3$;
1e is H, CN, SO$_2$R$^3$, or CO$_2$R$^3$, wherein each R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl; and
R$^2$ is H, substituted or unsubstituted aryl, substituted or unsubstituted heteroaryl; and the resulting fluorinated product has Formula II-A or II-B

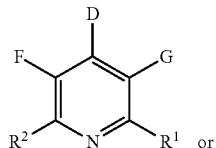

II-A

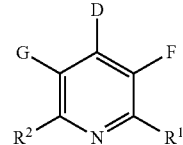

II-B wherein D is B or F; and G is C or F.

23. The method of claim 22, wherein the tetramethylammonium fluoride and the heteroaryl substrate are combined at from 10° C. to 60° C.

24. The method of claim 22, wherein the tetramethylammonium fluoride and the heteroaryl substrate are combined at from 20° C. to 40° C.

25. The method of claim 22, wherein the tetramethylammonium fluoride and the heteroaryl substrate are combined at room temperature.

26. The method of claim 22, wherein the tetramethylammonium fluoride and the heteroaryl substrate are combined for from 1 minute to 24 hours.

27. The method of claim 22, wherein the tetramethylammonium fluoride and the heteroaryl substrate are combined for from 1 minute to 3.5 hours.

28. The method of claim 22, wherein the tetramethylammonium fluoride and the heteroaryl substrate are combined in the presence of a solvent.

29. The method of claim 28, wherein the solvent is a polar aprotic solvent.

30. The method of claim 28, wherein the solvent is one or more of dimethylformamide, dimethylacetamide, sulfolane, dimethylsulfoxide, N-methylpyrrolidone, tetrahydrofuran, benzonitrile, or deuterated analogs thereof.

31. The method of claim 28, wherein the tetramethylammonium fluoride and the heteroaryl substrate are combined at about room temperature and the solvent is dimethylformamide.

32. The method of claim 22, wherein from 0.5 to 10 equivalents of the tetramethylammonium fluoride is used per equivalent of the heteroaryl substrate.

33. The method of claim 22, wherein from 1 to 2 equivalents of the tetramethylammonium fluoride is used per equivalent of the heteroaryl substrate.

34. The method of claim 22, wherein the tetramethylammonium fluoride is anhydrous.

35. The method of claim 22, wherein the tetramethylammonium fluoride and the heteroaryl substrate are combined in the presence of up to 2 equivalents of water per equivalent of the tetramethylammonium fluoride.

* * * * *

UNITED STATES PATENT AND TRADEMARK OFFICE
CERTIFICATE OF CORRECTION

PATENT NO. : 9,878,983 B2
APPLICATION NO. : 15/228188
DATED : January 30, 2018
INVENTOR(S) : Melanie Sanford et al.

Page 1 of 1

It is certified that error appears in the above-identified patent and that said Letters Patent is hereby corrected as shown below:

In the Claims

Column 36, Line 5, Claim 22, the term "le" should read --$R^1$--.

Signed and Sealed this
Twenty-seventh Day of March, 2018

Andrei Iancu
*Director of the United States Patent and Trademark Office*